(12) United States Patent
Lee

(10) Patent No.: US 9,362,507 B2
(45) Date of Patent: Jun. 7, 2016

(54) COMPOUND AND ORGANIC LIGHT-EMITTING DIODE INCLUDING THE SAME

(71) Applicant: Jung-Sub Lee, Yongin (KR)

(72) Inventor: Jung-Sub Lee, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 368 days.

(21) Appl. No.: 13/959,121

(22) Filed: Aug. 5, 2013

(65) Prior Publication Data

US 2014/0252324 A1    Sep. 11, 2014

(30) Foreign Application Priority Data

Mar. 5, 2013    (KR) .................. 10-2013-0023567

(51) Int. Cl.
| | |
|---|---|
| H01L 51/52 | (2006.01) |
| H01L 51/00 | (2006.01) |
| C07D 519/00 | (2006.01) |
| H01L 51/50 | (2006.01) |

(52) U.S. Cl.
CPC .......... H01L 51/0072 (2013.01); C07D 519/00 (2013.01); H01L 51/0071 (2013.01); H01L 51/0081 (2013.01); H01L 51/0085 (2013.01); H01L 51/5016 (2013.01)

(58) Field of Classification Search
None
See application file for complete search history.

(56) References Cited

U.S. PATENT DOCUMENTS

| | | |
|---|---|---|
| 2010/0289406 A1 | 11/2010 | Ma et al. |
| 2012/0193613 A1 | 8/2012 | Kadoma et al. |

FOREIGN PATENT DOCUMENTS

| | | |
|---|---|---|
| KR | 10-2011-0092262 A | 8/2011 |
| KR | 10-2011-0113297 A | 10/2011 |
| KR | 10-2012-0023780 A | 3/2012 |
| KR | 10-2012-0094838 A | 8/2012 |
| WO | WO 2011/126225 A1 | 10/2011 |

*Primary Examiner* — J. L. Yang
(74) *Attorney, Agent, or Firm* — Lee & Morse, P.C.

(57) ABSTRACT

Provided is an organic light-emitting diode including a compound of Formula 1 below:

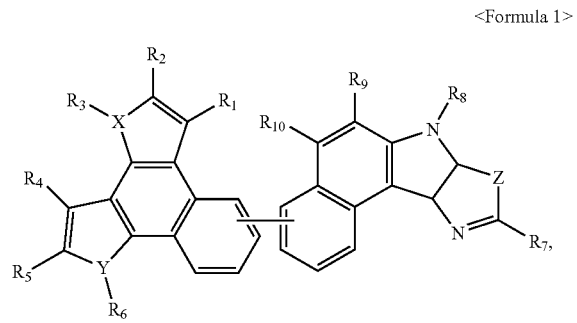

<Formula 1> wherein a detailed description of a substituent in Formula 1 above is defined as described in the detailed description.

20 Claims, 1 Drawing Sheet

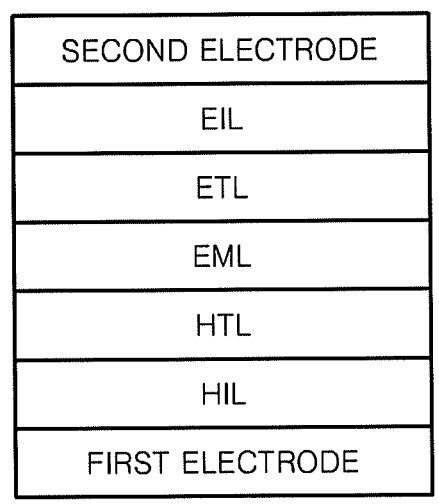

COMPOUND AND ORGANIC LIGHT-EMITTING DIODE INCLUDING THE SAME

CROSS-REFERENCE TO RELATED APPLICATION

This application claims the benefit of Korean Patent Application No. 10-2013-0023567, filed on Mar. 5, 2013, in the Korean Intellectual Property Office, the disclosure of which is incorporated herein in its entirety by reference.

BACKGROUND

1. Field

Embodiments relate to a compound and an organic light-emitting diode including the same.

2. Description of the Related Art

Organic light-emitting diodes (OLEDs), which are self-emitting diodes, have advantages such as wide viewing angles, excellent contrast, quick response, high brightness, and excellent driving voltage, and can provide multicolored images.

A typical diode has a structure including a substrate, an anode formed on the substrate, and a hole transport layer (HTL), an emission layer (EML), an electron transport layer (ETL), and a cathode which are sequentially stacked on the substrate. The HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons (carriers) recombine in the EML to generate excitons. When the excitons drop from an excited state to a ground state, light is emitted.

SUMMARY

Embodiments are directed to a compound represented by Formula 1 below:

<Formula 1>

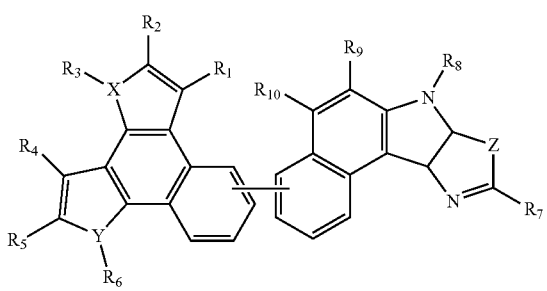

In Formula 1, $R_1$ to $R_{10}$ may each independently be a non-bonding electron pair, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group, and X, Y, and Z may each independently be N, S, or O.

$R_3$, $R_6$, $R_7$, and $R_8$ in Formula 1 may each independently be of the following compounds below:

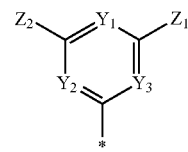

2a

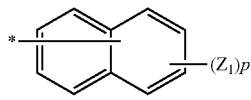

2b

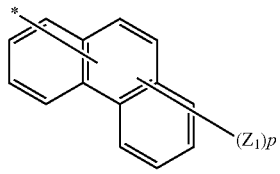

2c wherein, $Y_1$, $Y_2$, and $Y_3$ may each independently be CH or N;

$Z_1$ and $Z_2$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen atom, a cyano atom, a nitro group, a hydroxyl group, or a carboxyl group;

p may be an integer from 1 to 9; and

* is a binding site.

$R_1$, $R_5$, and $R_{10}$ in Formula 1 may each independently be a substituted or unsubstituted $C_1$-$C_{60}$ alkyl group.

$R_1$, $R_5$, and $R_{10}$ in Formula 1 may each independently be a t-butyl group or a methyl group.

$R_2$, $R_4$, and $R_9$ in Formula 1 may each independently be a hydrogen atom or a deuterium atom.

The compound of Formula 1 may be one of the following compounds below:

1

2
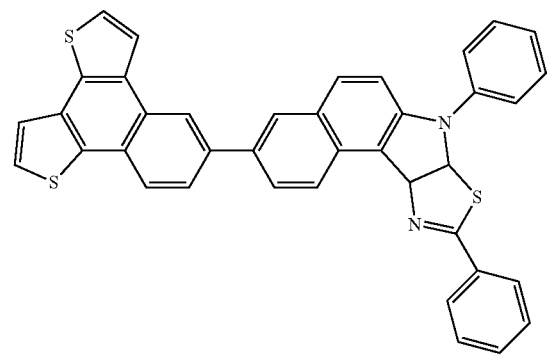
3
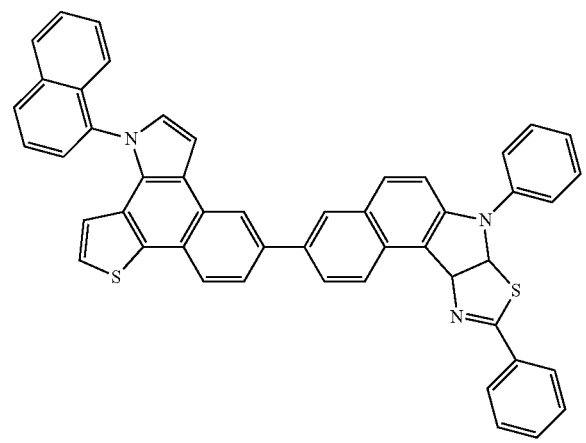
4
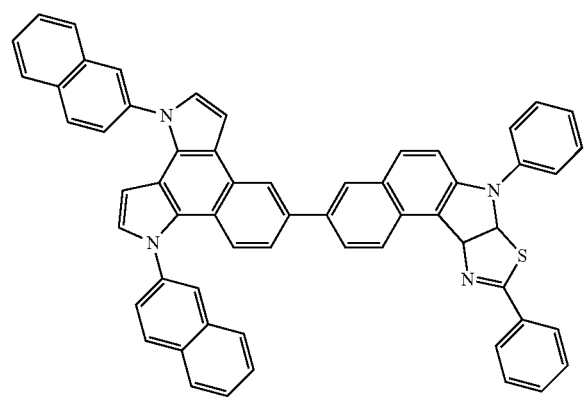
5
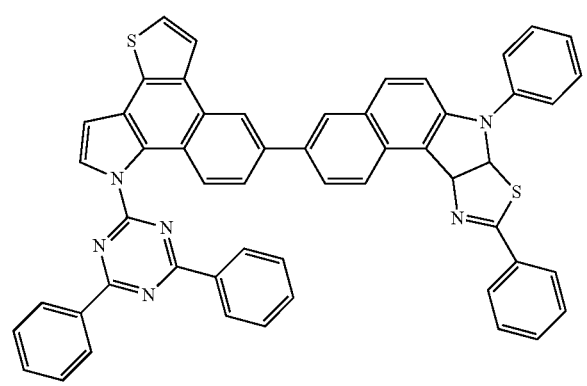
6
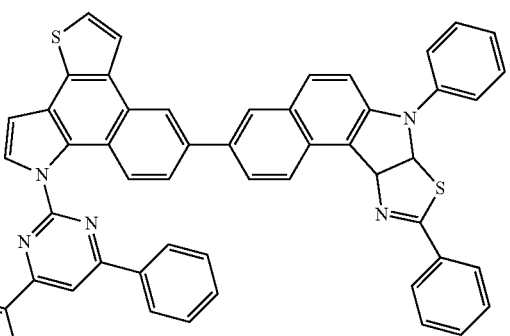
7
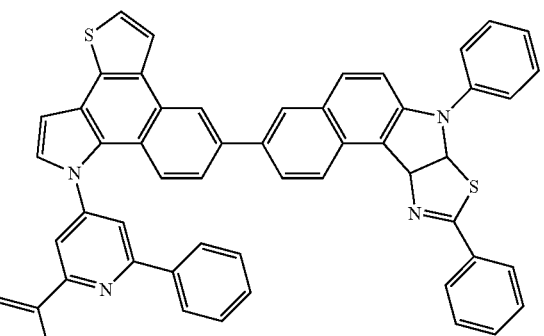
8
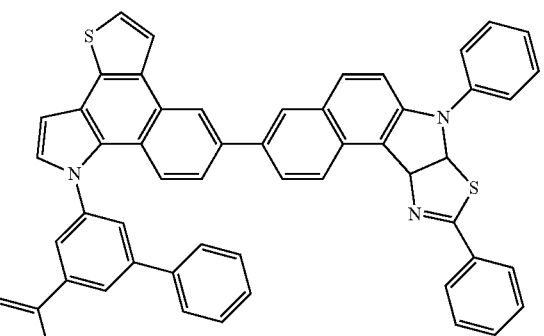
9
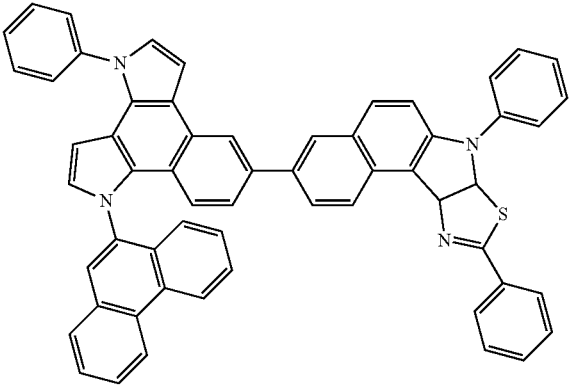

10
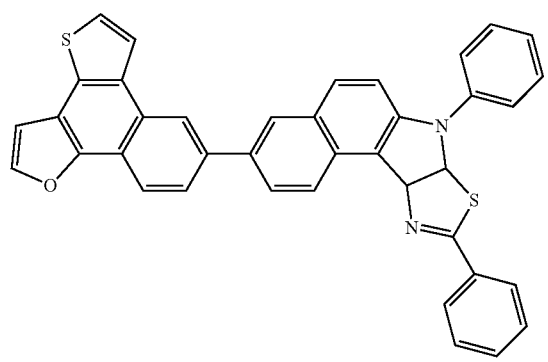
11
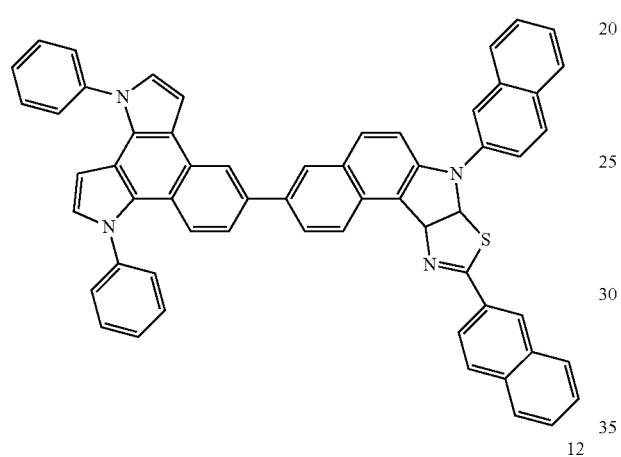
12
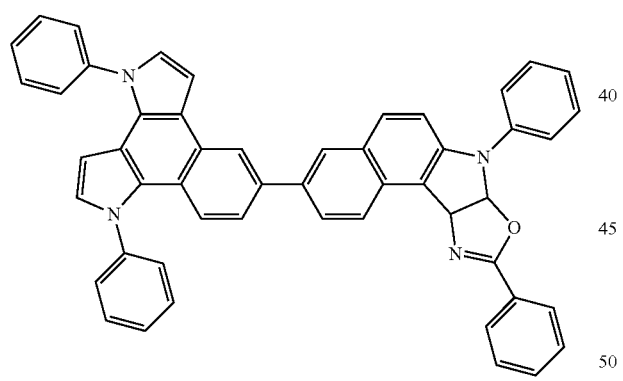
13
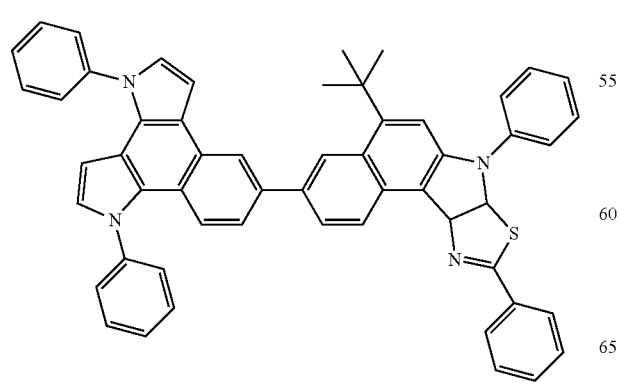
14
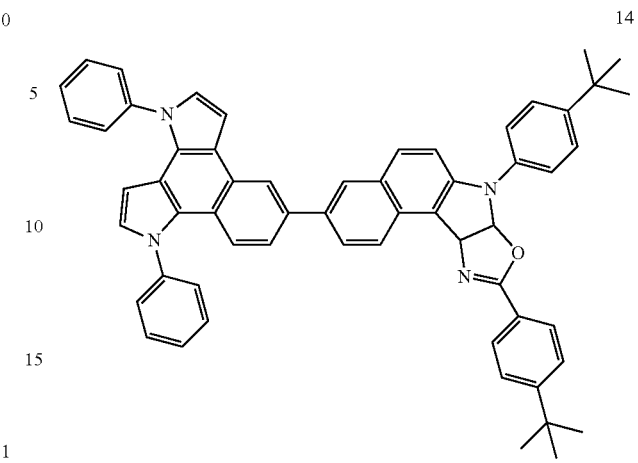
15
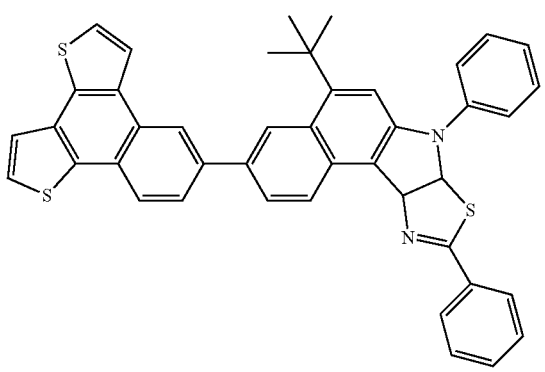
16
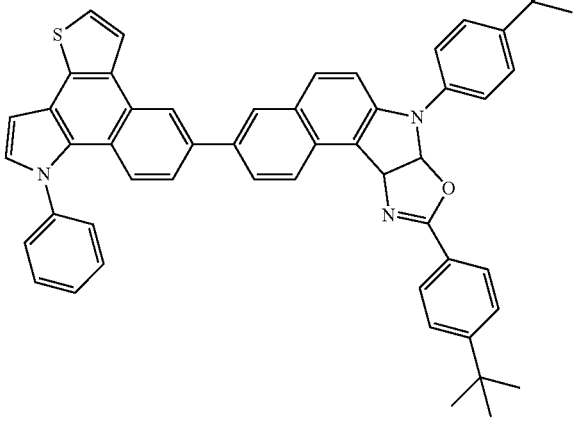

17
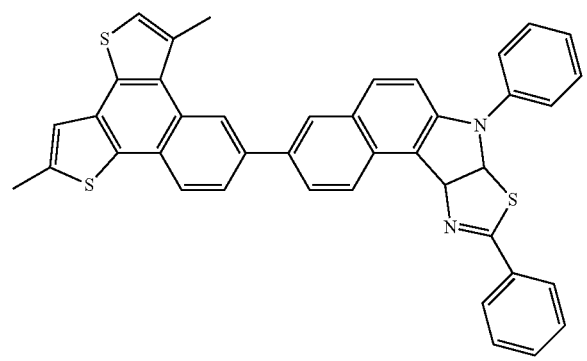
21
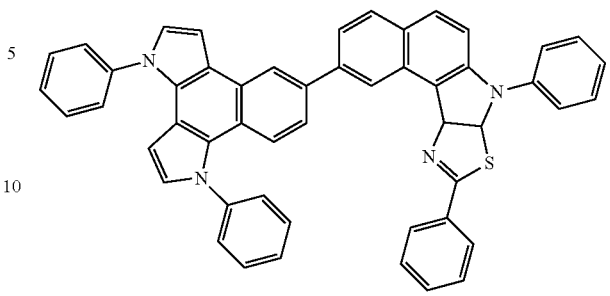
18
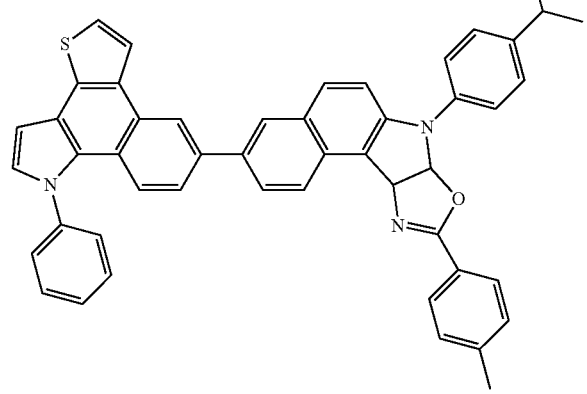
22
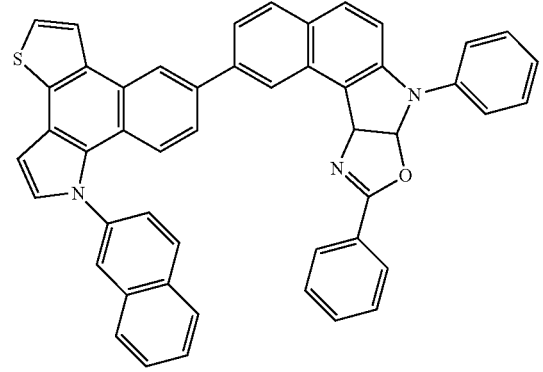
19
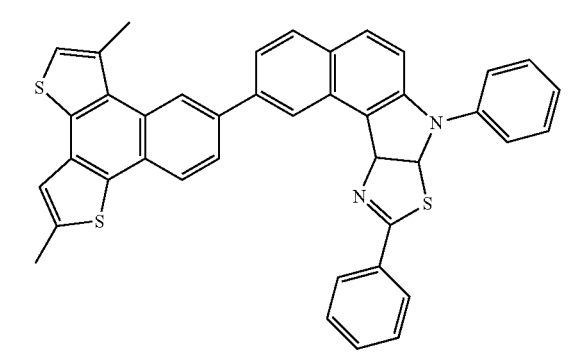
23
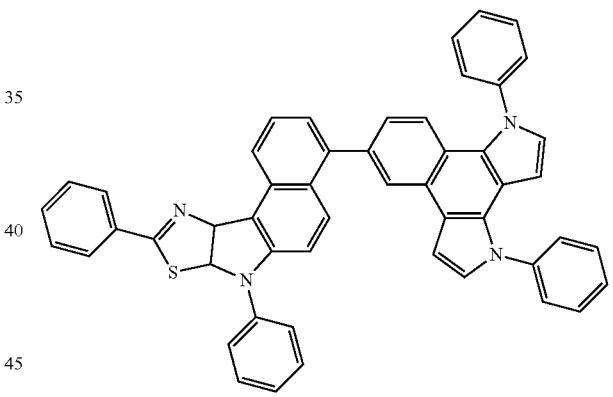
20
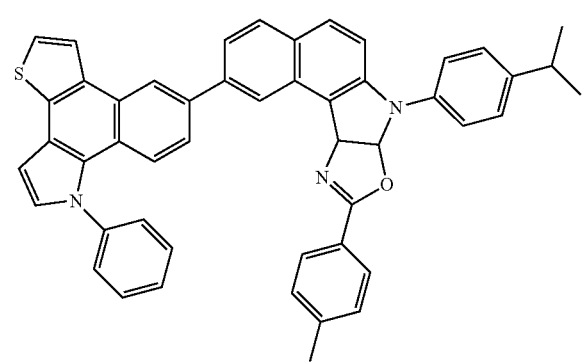
24
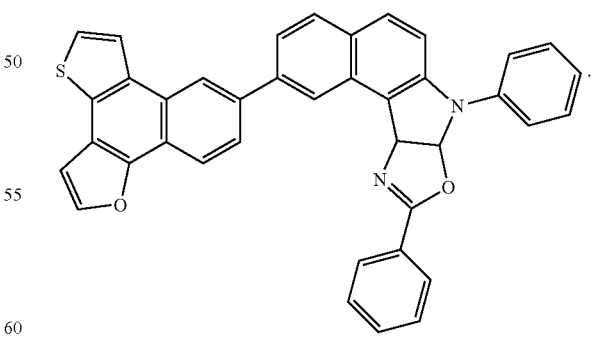
Embodiments are also directed to an organic light-emitting diode (OLED), including a first electrode; a second electrode; and an organic layer that is disposed between the first electrode and the second electrode, and includes a compound according to an embodiment.

The organic layer may be an emission layer.

The organic layer may be a green phosphorescent light-emitting layer.

The organic layer may be a green phosphorescent light-emitting layer, and the compound of Formula 1 may be used as a host.

The OLED may include an electron injection layer, an electron transport layer, a hole injection layer, a hole transport layer, or a functional layer having both hole injection and hole transport capabilities, and an emission layer that includes a compound according to an embodiment and an anthracene-based compound.

The OLED may include an electron injection layer, an electron transport layer, a hole injection layer, a hole transport layer, or a functional layer having both hole injection and hole transport capabilities, and an emission layer that includes a compound according to an embodiment and an arylamine-based compound.

The OLED may include an electron injection layer, an electron transport layer, a hole injection layer, a hole transport layer, or a functional layer having both hole injection and hole transport capabilities, and an emission layer that includes a compound according to an embodiment and a styryl-based compound.

The OLED may include an electron injection layer, an electron transport layer, a hole injection layer, a hole transport layer, or a functional layer having both hole injection and hole transport capabilities, and an emission layer. At least one of a red emission layer, a green emission layer, a blue emission layer, and a white emission layer of the emission layer may include a phosphorescent compound.

The hole injection layer, the hole transport layer, or the functional layer having both hole injection and hole transport capabilities may include a charge-generating material.

The charge-generating material may be a p-dopant, and the p-dopant may be a quinone derivative, a metal oxide, or a cyano group-containing compound.

The organic layer may include an electron transport layer, and the electron transport layer may include an electron-transporting organic compound and a metal complex.

The metal complex may be a lithium complex.

The organic layer may be formed of the compound of claim 1 by using a wet process.

Embodiments are also directed to a flat panel display device including an OLED according to an embodiment. The first electrode of the OLED may be electrically connected to a source electrode or a drain electrode in a thin film transistor.

BRIEF DESCRIPTION OF THE DRAWING

Features will become apparent to those of skill in the art by describing in detail example embodiments with reference to the attached drawing in which:

FIG. 1 is a schematic view of a structure of an organic light-emitting diode (OLED) according to an example embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey the scope of the example embodiments to those skilled in the art. In the drawing FIGURE, dimensions may be exaggerated for clarity of illustration. Like reference numerals refer to like elements throughout.

As used herein, the term "and/or" includes any and all combinations of one or more of the associated listed items. Expressions such as "at least one of" when preceding a list of elements, modify the entire list of elements and do not modify the individual elements of the list.

According to an example embodiment, there is provided a compound represented by Formula 1 below:

<Formula 1>

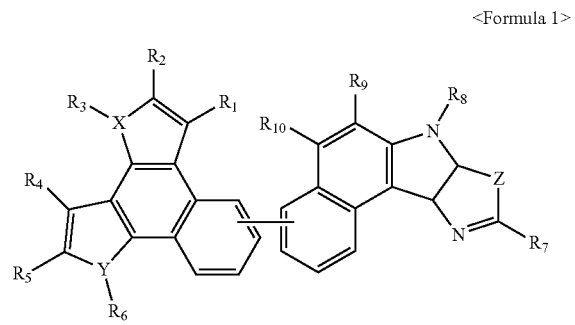

In Formula 1, $R_1$ to $R_{10}$ may each independently be a non-bonding electron pair, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group; and X, Y, and Z may each independently be N, S, or O.

The compound of Formula 1 according to the present example embodiment may have function as a green phosphorescent material for an organic-light emitting diode (OLED). Also, the compound of Formula 1 above may have a high glass transition temperature Tg or a melting point. Therefore, in regard to the OLED, the compound of Formula 1 above may increase the thermal resistance thereof, e.g., increase the resistance thereof to high-temperature against Joule heat that is generated in an organic layer, between organic layers, or between an organic layer and a metal electrode. The OLED manufactured using the heterocyclic compound according to the present example embodiment may have a large effect on increasing advantages such as high durability during storage or operation.

The substituents in the compound of Formula 1 above will now be described in more detail.

In some embodiments, $R_3$, $R_6$, $R_7$, and $R_8$ in Formula 1 may be one of the following compounds below:

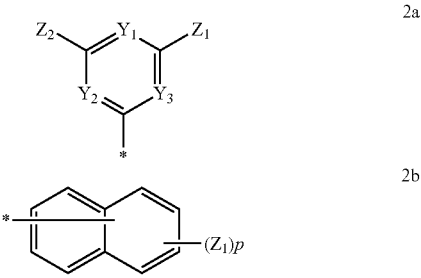

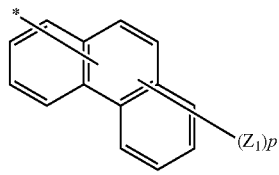

2c wherein, $Y_1$, $Y_2$, and $Y_3$ may each independently be CH or N;

$Z_1$ and $Z_2$ may each independently be a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, and an amino group substituted with a $C_6$-$C_{20}$ aryl group or a $C_3$-$C_{20}$ heteroaryl group, a halogen atom, a cyano atom, a nitro group, a hydroxyl group, or a carboxyl group;

p may be an integer from 1 to 9; and * is a binding site.

In some other embodiments, $R_1$, $R_5$, and $R_{10}$ in Formula 1 may be a substituted or unsubstituted $C_1$-$C_{60}$ alkyl group, e.g., $R_1$, $R_5$, and $R_{10}$ may each independently be a t-butyl group or a methyl group.

In some other embodiments, $R_2$, $R_4$, and $R_9$ in Formula 1 may each independently be a hydrogen atom or a deuterium atom:

Hereinafter, the definition of representative substituents used herein will be described in detail. (In this regard, numbers of carbons limiting a substituent are non-limited, and thus the substituent characteristics are not limited).

The unsubstituted $C_1$-$C_{60}$ alkyl group used herein may be linear or branched. Non-limiting examples of the unsubstituted $C_1$-$C_{60}$ alkyl group are a methyl group, an ethyl group, a propyl group, an iso-butyl group, a sec-butyl group, a pentyl group, an iso-amyl group, a hexyl group, a heptyl group, an octyl group, a nonanyl group, and a dodecyl group. At least one hydrogen atom of the unsubstituted $C_1$-$C_{60}$ alkyl group may be substituted with a deuterium atom, a halogen atom, a hydroxyl group, a nitro group, a cyano atom, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsubstituted alkenyl group having at least one carbon-carbon double bond in the center or at a terminal thereof. Examples of the unsubstituted $C_2$-$C_{60}$ alkenyl group are an ethenyl group, a propenyl group, a butenyl group, and the like. At least one hydrogen atom of the unsubstituted alkenyl group may be substituted with the same substituent as used in the substituted alkyl group described above.

The unsubstituted $C_2$-$C_{60}$ alkynyl group indicates an unsubstituted alkynyl group having at least one carbon-carbon triple bond in the center or at a terminal of thereof. Examples of the unsubstituted $C_2$-$C_{60}$ alkynyl group are acetylene, propylene, phenylacetylene, naphthylacetylene, isopropylacetylene, t-butylacetylene, diphenylacetylene, and the like. At least one hydrogen atom of the unsubstituted $C_2$-$C_{60}$ alkynyl group may be substituted with the same substituent as used in the substituted alkyl group.

The unsubstituted $C_3$-$C_{60}$ cycloalkyl group indicates an alkyl group in the form of $C_3$-$C_{60}$ rings, and at least one hydrogen atom of the $C_3$-$C_{60}$ cycloalkyl group may be substituted with the same substituent with the same substituent as used in the $C_1$-$C_{60}$ alkyl group.

The unsubstituted $C_1$-$C_{60}$ alkoxy group has a structure of —OA (wherein, A is an unsubstituted $C_1$-$C_{60}$ alkyl group described above). Non-limiting examples of the unsubstituted $C_1$-$C_{60}$ alkoxy group are a methoxy group, an ethoxy group, a propoxy group, an isopropyloxy group, a butoxy group, a pentoxy group, and the like. At least one hydrogen atom of the unsubstituted alkoxy group may be substituted with the same substituent as used in the substituted alkyl group.

The unsubstituted $C_6$-$C_{60}$ aryl group indicates a carbocyclic aromatic system including at least one ring. When the unsubstituted $C_6$-$C_{60}$ aryl group has two or more of rings, the rings may be fused or linked to each other by a single bond. The term 'aryl' refers to an aromatic system such as phenyl, naphthyl, and anthracenyl. Also, at least one hydrogen atom of the aryl group may be substituted with the same substituent as used in the $C_1$-$C_{60}$ alkyl group.

Examples of the substituted or unsubstituted $C_6$-$C_{60}$ aryl group are a phenyl group, a $C_1$-$C_{10}$ alkylphenyl group (i.e., an ethylphenyl group), a halophenyl group (i.e., an o-, m-, and p-fluorophenyl group and a dichlorophenyl group), a cyanophenyl group, a dicyanophenyl, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m-, and p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (i.e., a fluoronaphthyl group), a $C_1$-$C_{10}$ alkylnaphthyl group (i.e., a methylnaphthyl group), a $C_1$-$C_{10}$ alkoxynaphthyl group (i.e., a methoxynaphthyl group), a cyanonaphthyl group, an anthracenyl group, an azulenyl group, a heptalenyl group, an acenaphtylenyl group, a phenalenyl group, a fluorenyl group, an anthraquinolyl group, a methylanthryl group, a phenanthryl group, a triphenylene group, a pyrenyl group, a chrycenyl group, an ethylchrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphtylenyl group, a heptaphenyl group, a heptacenyl group, a pyranthrenyl group, an ovalenyl group, and the like.

The unsubstituted $C_3$-$C_{60}$ heteroaryl group used herein may include one, two, or three hetero atoms selected from N, O, P, or S. Examples of the unsubstituted $C_4$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group, and the like. In addition, at least one hydrogen atom of the heteroaryl group may be substituted with the same substituent as used in the unsubstituted $C_1$-$C_{60}$ alkyl group.

The unsubstituted $C_6$-$C_{60}$ aryloxy group is a group represented by —$OA_1$, wherein $A_1$ is a $C_6$-$C_{60}$ aryl group. Examples of the aryloxy group are a phenoxy group, and the like. At least one hydrogen atom of the aryloxy group may be substituted with the same substituent as used in the unsubstituted $C_1$-$C_{60}$ alkyl group.

The unsubstituted $C_6$-$C_{60}$ arylthio group is a group represented by —$SA_1$, wherein $A_1$ is a $C_6$-$C_{60}$ aryl group. Examples of the arylthio group are a benzylthio group, a naphthylthio group, and the like. At least one hydrogen atom of the arylthio group may be substituted with the same substituent as used in the unsubstituted $C_1$-$C_{60}$ alkyl group.

The unsubstituted $C_6$-$C_{60}$ condensed polycyclic group used herein refers to a substituent including at least two rings, wherein at least one aromatic ring and at least one non-aromatic ring are fused to each other, or a substituent having an unsaturated group within a ring but being unable to form a conjugated structure. Therefore, the unsubstituted $C_6$-$C_{60}$ condensed polycyclic group is distinct from the aryl or the heteroaryl groups in terms of being non-aromatic.

Examples of the compound of Formula 1 according to the present example embodiment are the following compounds below, but are not limited thereto:

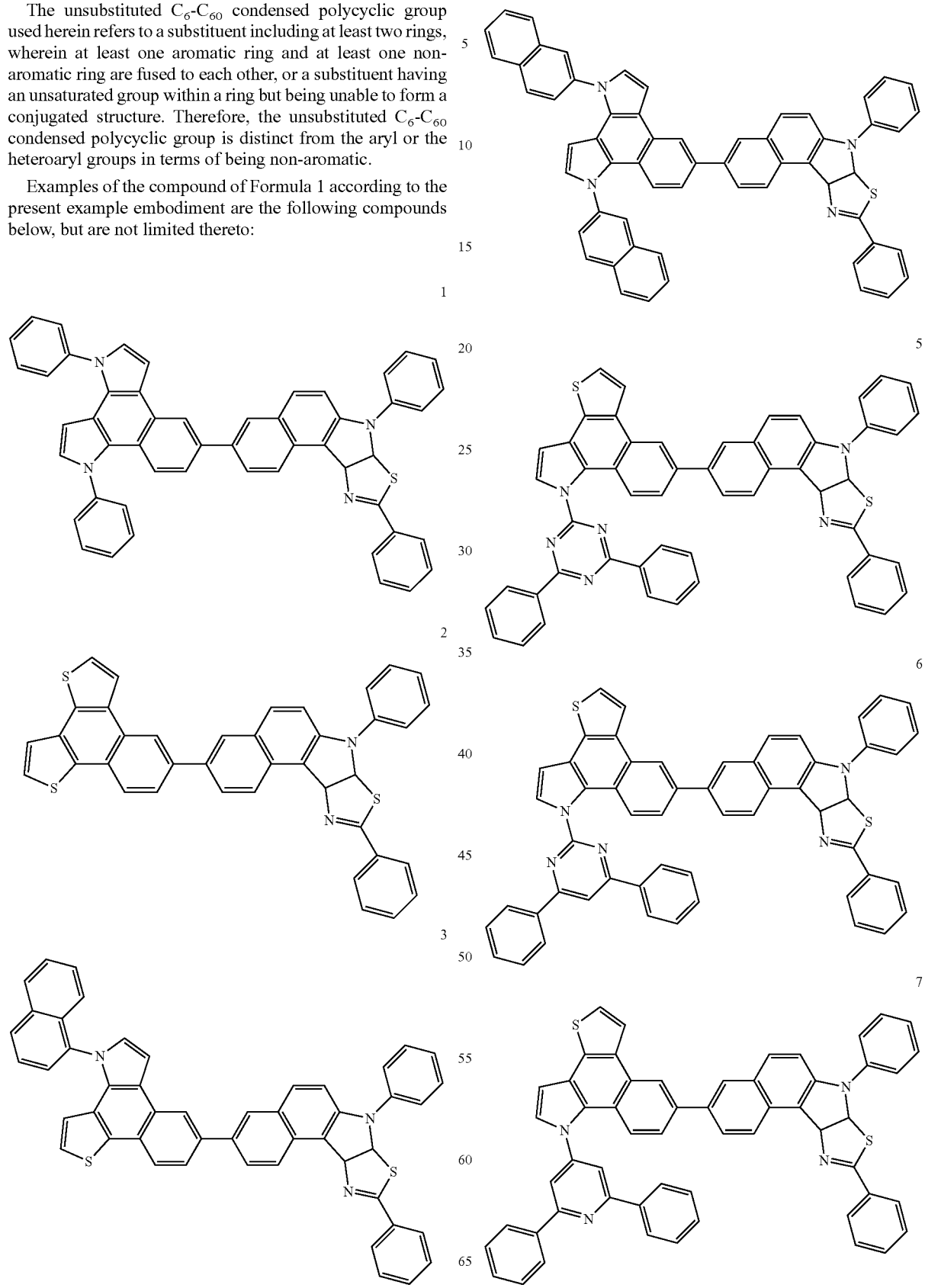

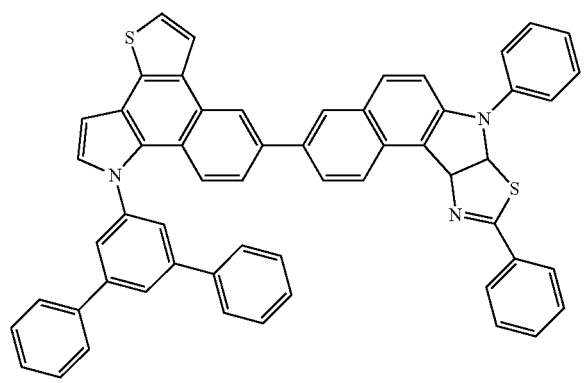
8
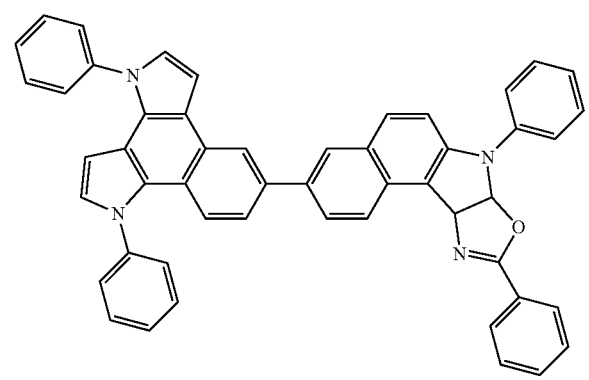
12
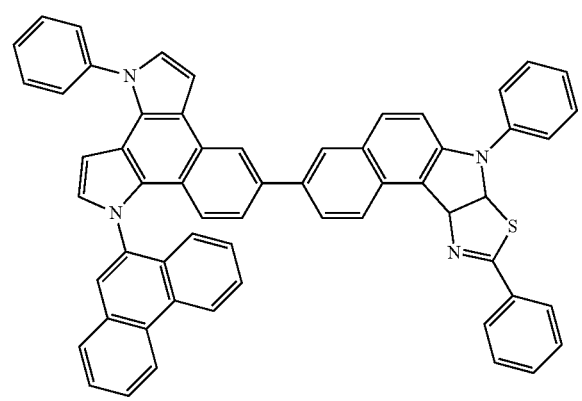
9
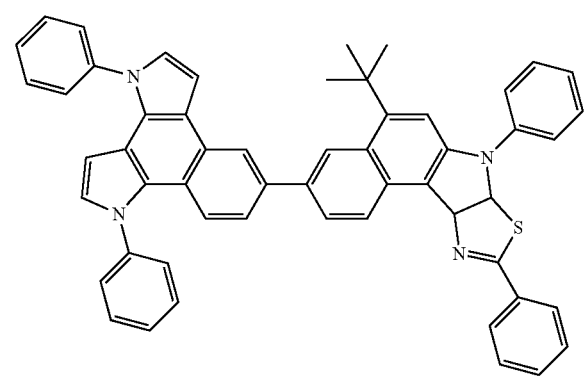
13
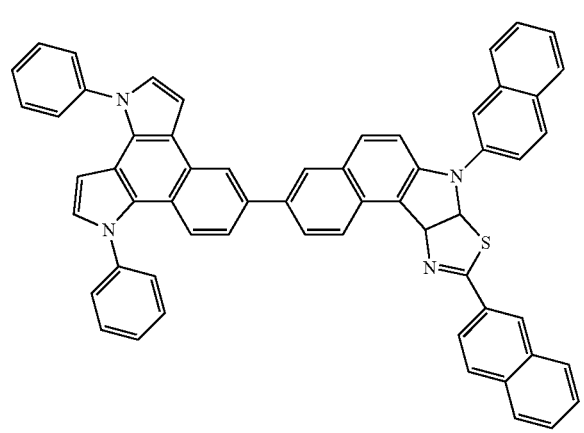
10
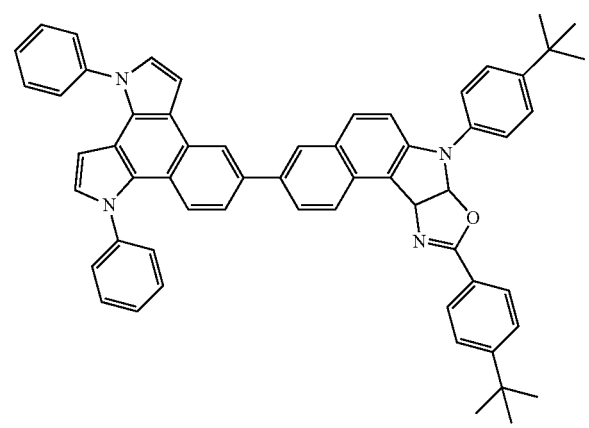
14
11
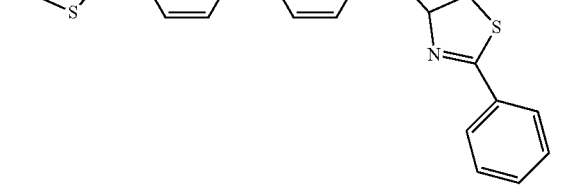
15

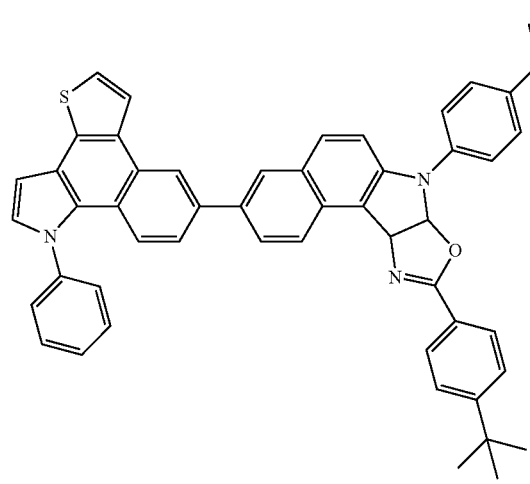
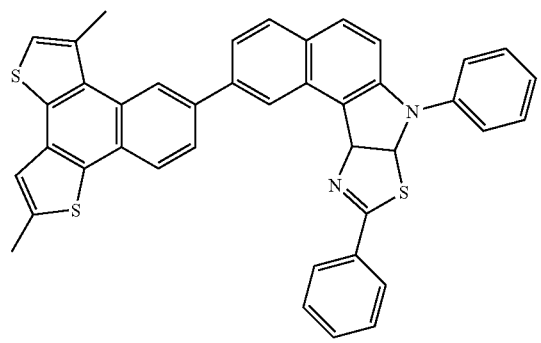

-continued

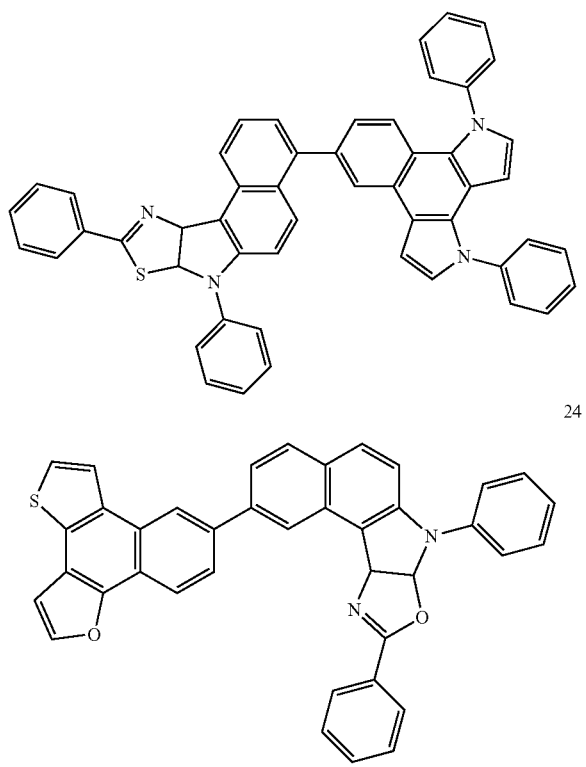

According to another example embodiment, an OLED includes a first electrode; a second electrode; and an organic layer that is disposed between the first electrode and the second electrode and includes the compound of Formula 1 above.

The organic layer may include at least one layer selected from a hole injection layer (HIL), a hole transport layer (HTL), a functional layer having both hole injection and hole transport capabilities (hereinafter, referred as a "H-functional layer"), a buffer layer, an electron blocking layer (EBL), an emission layer (EML), a hole blocking layer (HBL), an electron transport layer (ETL), an electron injection layer (EIL), and a functional layer having both electron injection and electron transport capabilities (hereinafter, referred as an "E-functional layer").

In greater detail, the organic layer may be an EML, and for example, the compound according to an embodiment may be used as a host for a phosphorescent layer of green color.

In some embodiments, the OLED may include an EIL, an ETL, an EML, a HIL, a HTL, or a H-functional layer having both hole injection and hole transport capabilities. The EML may include the compound of the Formulas above; and an anthracene-based compound, an arylamine-based compound, or a styryl-based compound.

In some other embodiments, the OLED may include an EIL, an ETL, an EML, a HIL, a HTL, or a H-functional layer having both hole injection and hole transport capabilities, wherein at least one of a red EML, a green EML, a blue EML, and a white EML of the EML may include a phosphorescent compound, and the HIL, the HTL, or the H-functional layer having both hole injection and hole transport capabilities may include a charge-generating material. The charge-generating material may be a p-dopant, and the p-dopant may be a quinone derivative, a metal oxide, or a cyano group-containing compound.

In some other embodiments, the organic layer may include an ETL, and the ETL may include an electron-transporting organic compound and a metal complex. The metal complex may be a lithium (Li) complex.

The term "organic layer" used herein refers to a single layer and/or a multi-layer disposed between the first electrode and the second electrode of the OLED.

The organic layer may include an EML, and the EML may include the compound of the Formulas above. In some embodiments, the organic layer may include at least one layer of a HIL, a HTL, a H-functional layer having both hole injection and hole transport capabilities, and at least one layer of the HIL, the HTL, and the H-functional layer having both hole injection and hole transport capabilities may include the compound of the Formulas above.

FIG. 1 is a schematic view of a structure of an OLED according to an example embodiment. Hereinafter, a structure and a manufacturing method of an OLED according to an example embodiment will be described in detail with reference to FIG. 1.

A substrate (not illustrated), which may be a substrate suitable for use in a general OLED, may be a glass substrate or a transparent plastic substrate with excellent mechanical strength, thermal stability, transparency, surface smoothness, ease of handling, and water resistance.

A first electrode may be formed by depositing or sputtering a material for a first electrode on the substrate. When the first electrode is an anode, the material for the first electrode may be selected from materials with a high work function to enable ease of hole injection. The first electrode may be a reflective electrode or a transmission electrode. The material for the first electrode may be a transparent material with high conductivity, and examples thereof are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be used as a reflective electrode.

The first electrode may have a single-layer structure or a multi-layer structure including at least two layers. For example, the first electrode may have a three-layered structure of ITO/Ag/ITO, but is not limited thereto.

The organic layer may be disposed on the first electrode.

The organic layer may include a HIL, a HTL, a buffer layer (not illustrated), an EML, an ETL, or an EIL.

An HIL may be formed on the first electrode by using various methods such as vacuum deposition, spin coating, casting, and Langmuir-Blodgett (LB) deposition.

When the HIL is formed using vacuum deposition, vacuum deposition conditions may vary depending on the compound that is used to form the HIL, and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary depending on the compound that is used to form the HIL, and the desired structure and thermal properties of the HIL to be formed. For example, the coating rate may be in a range from about 2,000 rpm to about 5,000 rpm, and a temperature at which heat treatment is performed to remove a solvent after coating may be in a range from about 80° C. to about 200° C. However, the coating conditions are not limited thereto.

As a material for the HIL, a general hole-injecting material, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS) may be used, but the hole-injecting material is not limited thereto:

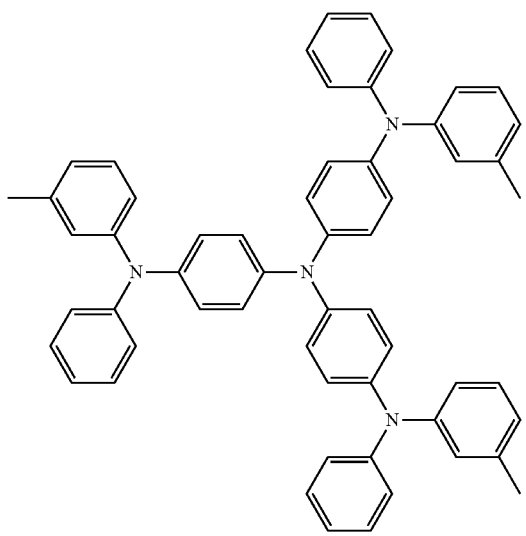

m-MTDATA

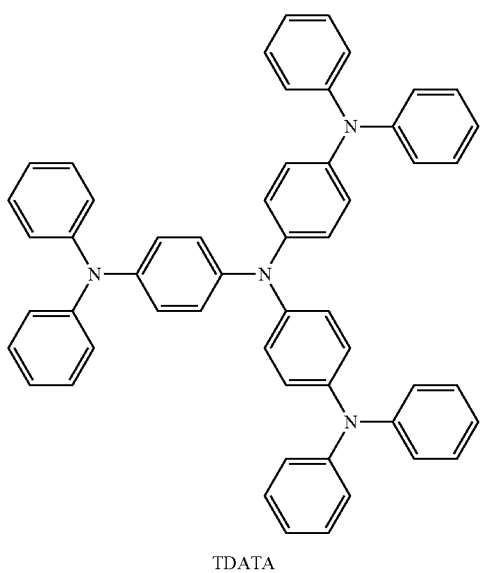

TDATA

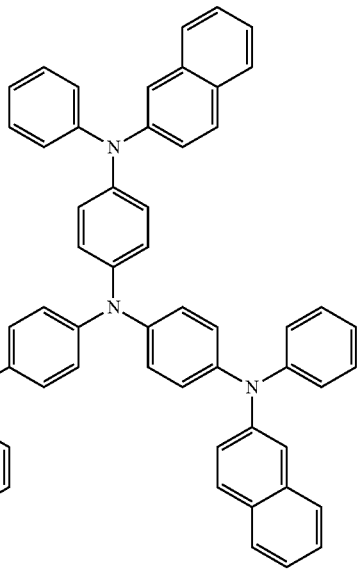

2-TNATA

A thickness of the HIL may be in a range from about 100 Å to about 10,000 Å, for example, from about 100 Å to about 1,000 Å. When the thickness of the HIL is within the above ranges, the HIL may have satisfactory hole injection characteristics without a substantial increase in a driving voltage.

Then, an HTL may be formed on the HIL by using vacuum deposition, spin coating, casting, LB deposition, or the like. When the HTL is formed using vacuum deposition or spin coating, the deposition and coating conditions may be similar to those for the formation of the HIL, although the deposition and coating conditions may vary depending on a compound that is used to form the HTL.

As a material for the HTL, a general hole-transporting material, for example, a carbazole derivative such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine) (TCTA), and N,N'-di(1-naphthyl)-N,N'-diphenylbenzidine (NPB) may be used, but the hole-transporting material is not limited thereto:

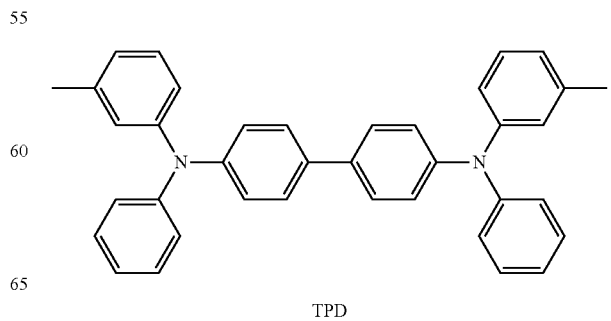

TPD

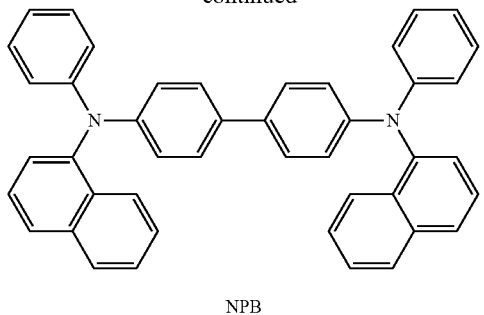

NPB

A thickness of the HTL may be in a range from about 50 Å to about 2,000 Å, for example, from about 100 Å to about 1,500 Å. When the thickness of the HTL is within the above ranges, the HTL may have satisfactory hole transport characteristics without a substantial increase in a driving voltage.

The H-functional layer (a functional layer having both hole injection and hole transport capabilities) may include one or more materials selected from the above-described materials for the HIL and the HTL. A thickness of the H-functional layer may be in a range from about 500 Å to about 10,000 Å, for example, from about 100 Å to about 1,000 Å. When the thickness of the H-functional layer is within the above ranges, the H-functional layer may have satisfactory hole injection and transport characteristics without a substantial increase in a driving voltage.

In some embodiments, at least one layer of the HIL, the HTL, and the H-functional layer may include at least one of the following compounds represented by Formulas 300 and 350 below:

<Formula 300>

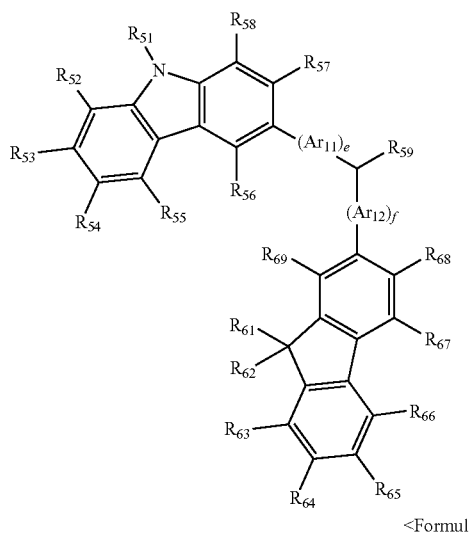

<Formula 350>

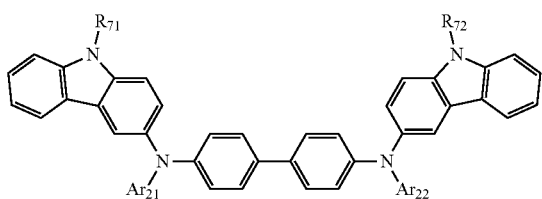

$Ar_{11}$, $Ar_{12}$, $Ar_{21}$, and $Ar_{22}$ in Formulas 300 and 350 may each independently be a substituted or unsubstituted $C_5$-$C_{60}$ arylene group.

e and f in Formula 300 may each independently be an integer from 0 to 5, for example, 0, 1, or 2. In some embodiments, e may be 1 and f may be 0, but are not limited thereto.

$R_{51}$ to $R_{58}$, $R_{61}$ to $R_{69}$, $R_{71}$, and $R_{72}$ in Formulas 300 and 350 may each independently be a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, $R_{71}$, and $R_{72}$ may each independently be selected from a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid or a salt thereof; a phosphoric acid or a salt thereof; a $C_1$-$C_{10}$ alkyl group (i.e., a methyl group, an ethyl group, a propyl group, a butyl group, a pentyl group, a hexyl group, or the like); a $C_1$-$C_{10}$ alkoxy group (i.e., a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;

a phenyl group; a naphthyl group; an anthryl group; a fluorenyl group; a pyrenyl group; and a phenyl group, a naphthyl group, an anthryl group, a fluorenyl group, and a pyrenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but is not limited thereto.

$R_{59}$ in Formula 300 may be selected from a phenyl group; a naphthyl group; an anthryl group; a biphenyl group; a pyridyl group; and a phenyl group, a naphthyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

In some embodiments, the compound of Formula 300 may be represented by 300A below, but the compound is not limited thereto:

<Formula 300A>
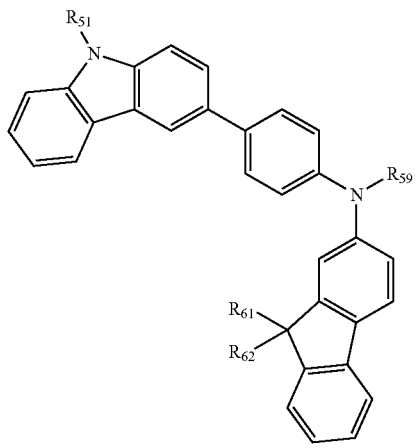
A detailed description of $R_{51}$, $R_{62}$ $R_{61}$, and $R_{59}$ in Formula 300A has already been described above.
For example, at least one layer of the HIL, HTL, and the H-functional layer may include at least one of the following Compounds 301 to 320, but is not limited thereto:
301
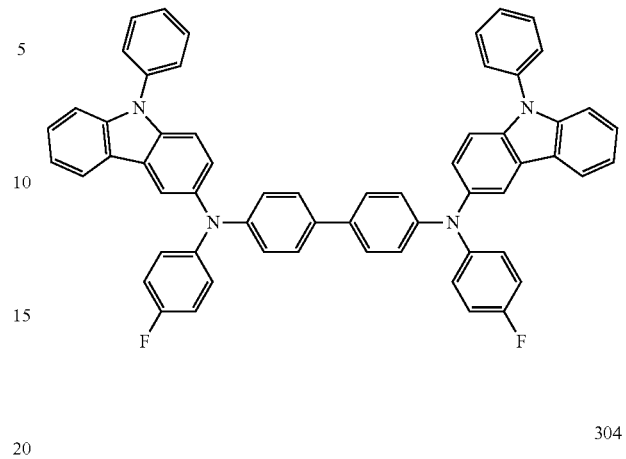
303
304
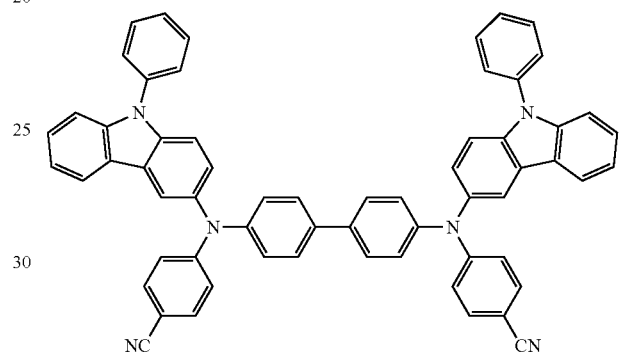
305
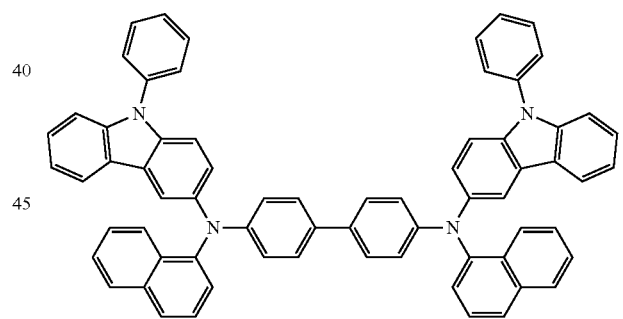
306
302
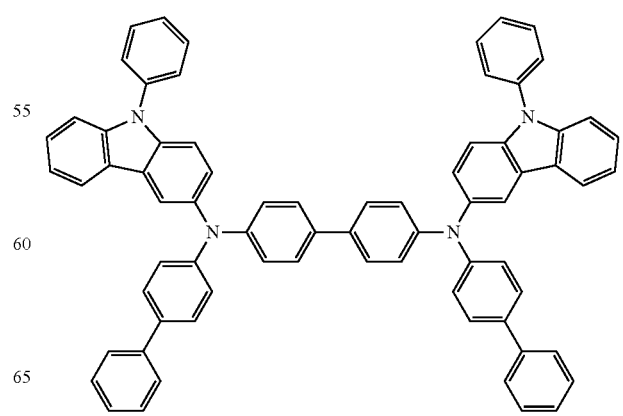

27
-continued
307
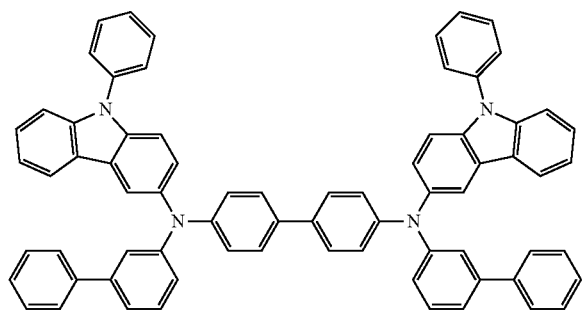
308
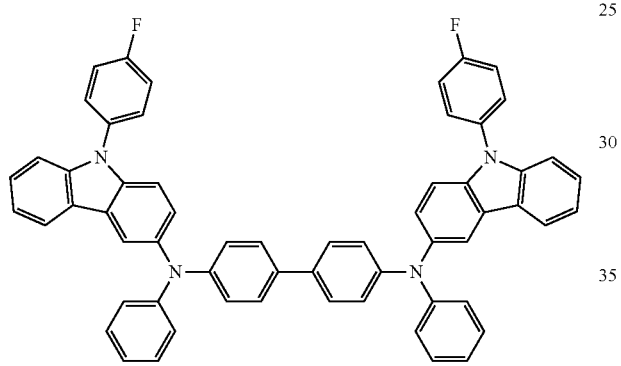
28
-continued
310
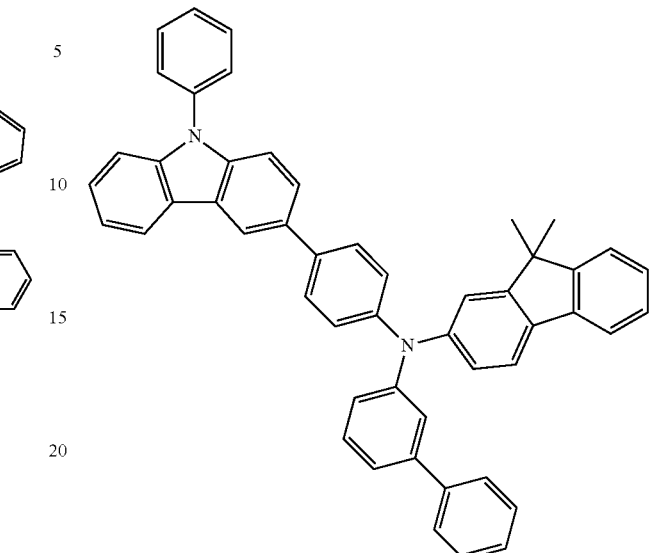
309
311
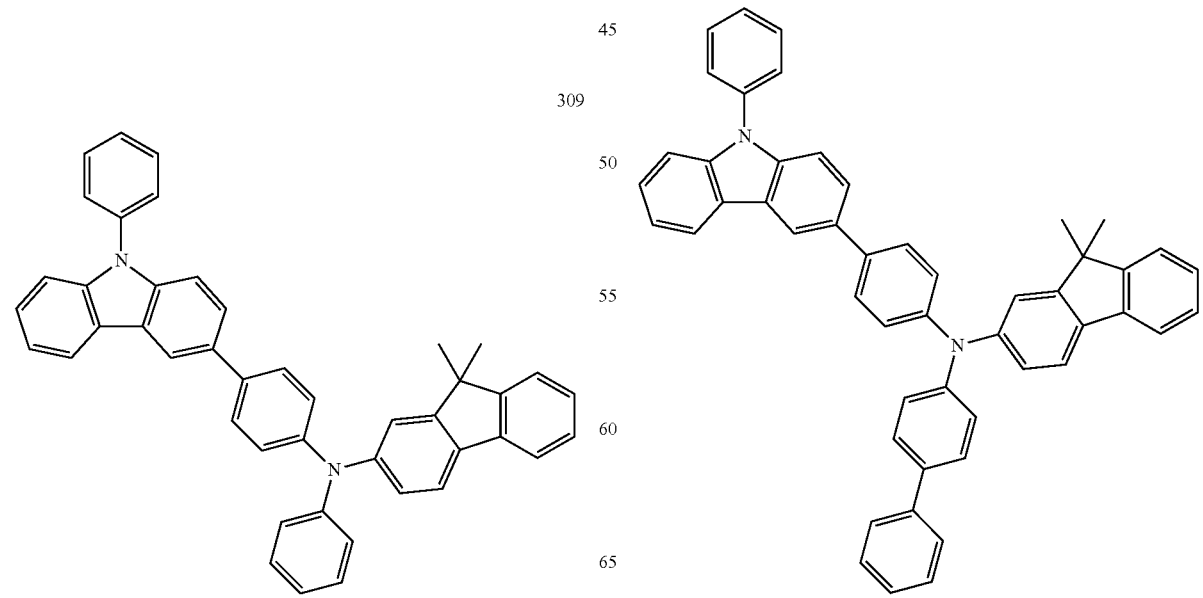

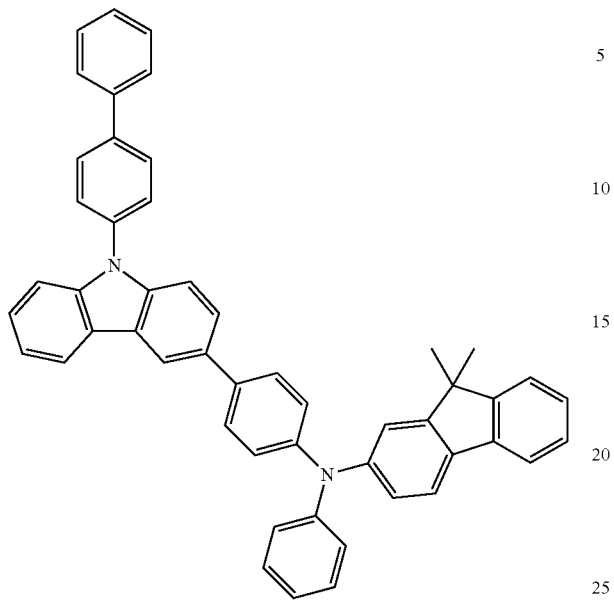
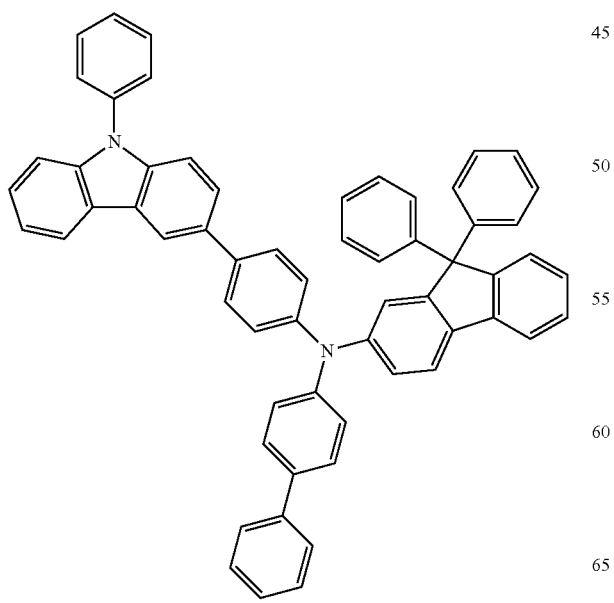

31
-continued

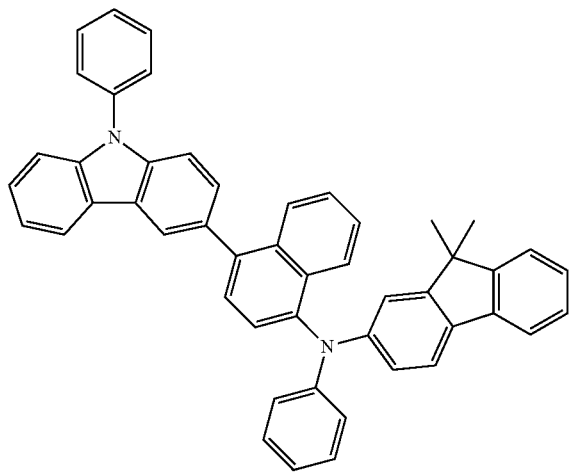

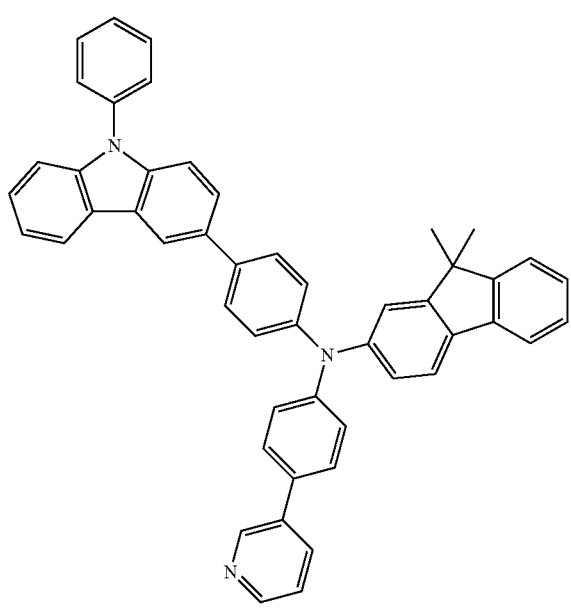

32
-continued

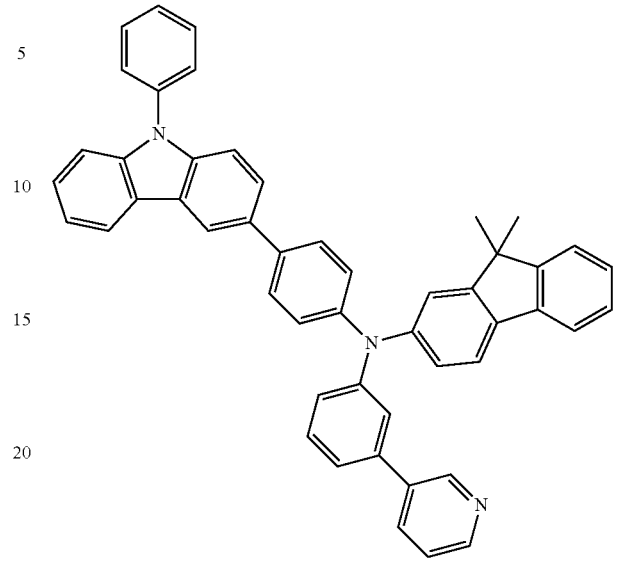

At least one layer of the HIL, HTL, and the H-functional layer may further include a charge-generating material to improve conductivity of a film, in addition to such general hole-injecting materials, general hole-transporting materials, and/or general H-functional materials having both hole injection and hole transport capabilities.

The charge-generating material may be, for example, a p-dopant. The p-dopant may be one of a quinone derivative, a metal oxide, and a compound with a cyano group, but is not limited thereto. Non-limiting examples of the p-dopant are quinone derivatives such as tetracyanoquinodimethane (TCNQ) and 2,3,5,6-tetrafluoro-tetracyano-1,4-benzoquinodimethane (F4-TCNQ); metal oxides such as a tungsten oxide and a molybdenum oxide; and cyano group-containing compounds such as Compound 200 below, but are not limited thereto:

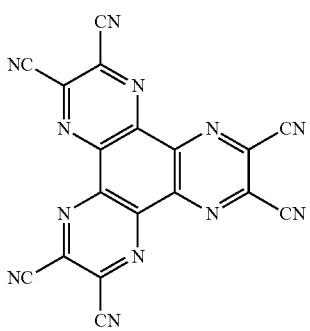

<Formula 200>

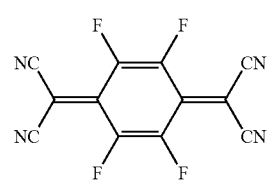

<F4-TCNQ>

When the HIL, the HTL, or the H-functional layer further includes the charge-generating material, the charge-generating material may be homogeneously dispersed or non-homogeneously distributed in the layers above.

A buffer layer may be disposed between at least one of the HIL, HTL, and the H-functional layer, and the EML. The buffer layer may compensate for an optical resonance distance of light according to a wavelength of the light emitted from the EML, and thus may increase efficiency. The buffer layer may include a suitable hole injecting material or hole transporting material. In some other embodiments, the buffer layer may include the same material as one of the materials included in the HIL, the HTL, and the H-functional layer that underlie the buffer layer.

Then, an EML may be formed on the HIL, the H-functional layer, or the buffer layer by vacuum deposition, spin coating, casting, LB deposition, or the like. When the EML is formed using vacuum deposition or spin coating, the deposition and coating conditions may be similar to those for the formation of the HIL, although the conditions for deposition and coating may vary depending on the material that is used to form the EML.

The EML maybe formed using a variety of suitable light-emitting materials, for example, a general host and a general dopant, in addition to the compound of Formula 1 as described above. In regard to the dopant, both a general fluorescent dopant and a general phosphorescent dopant may be used Examples of the general host are $Alq_3$, 4,4'-N,N'-dicarbazole-biphenyl (CBP), poly(n-vinylcarbazole) (PVK), 9,10-di(naphthylene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (see Formula below), and Compounds 501 to 509 below, but are not limited thereto.

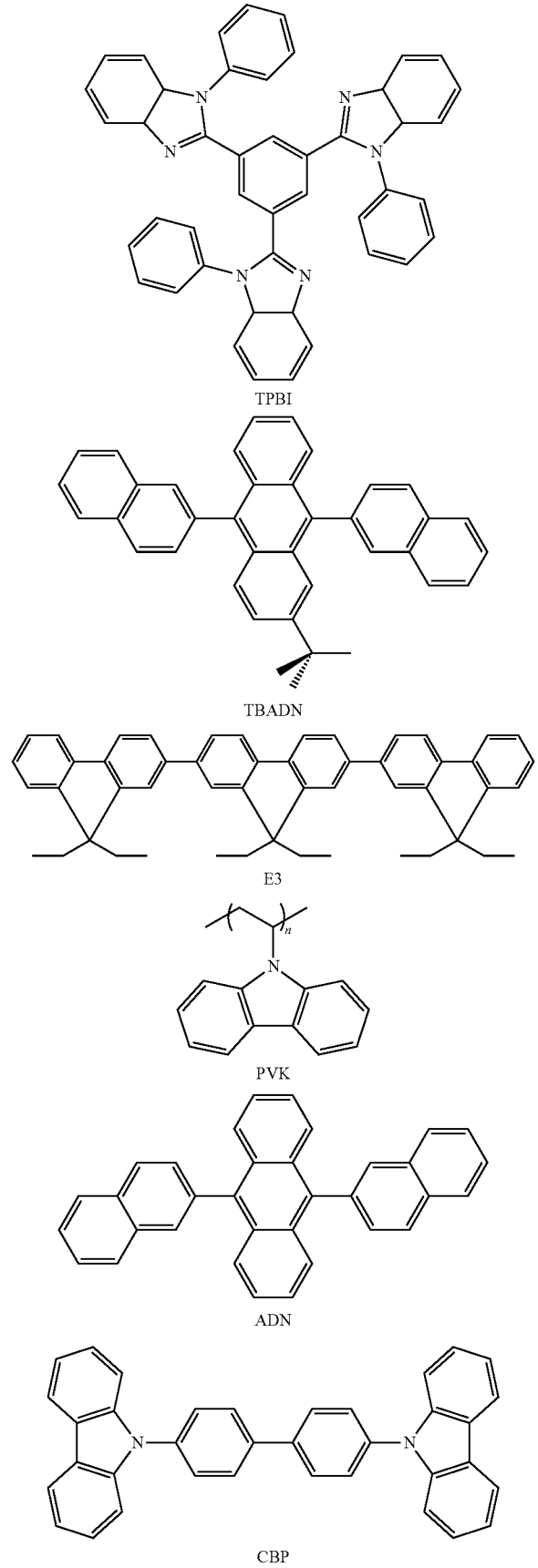

35
-continued
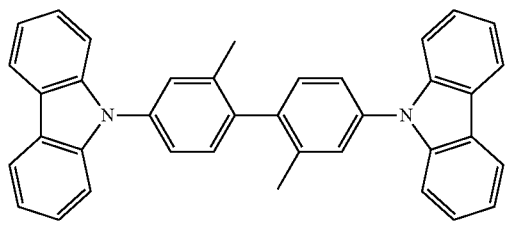
dmCBP
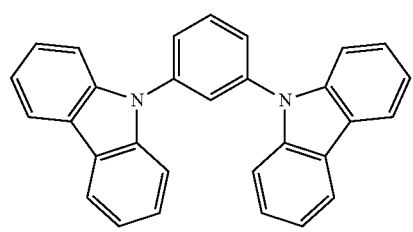
501
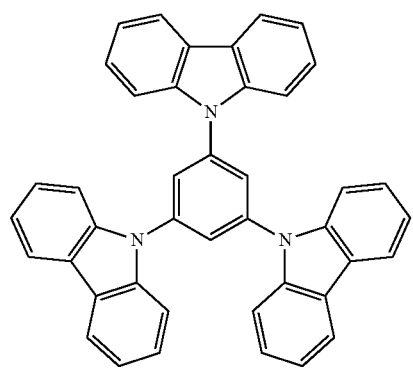
502
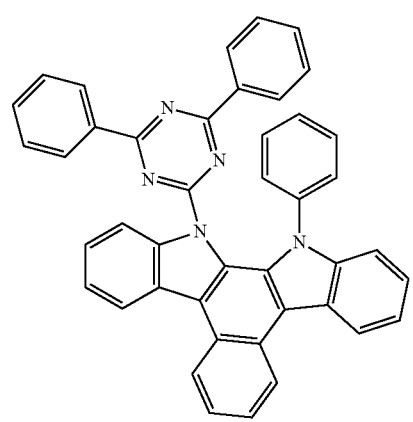
503
36
-continued
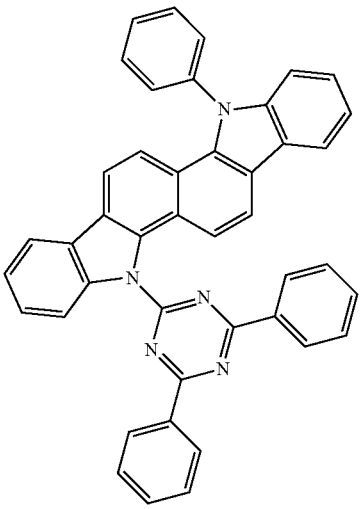
504
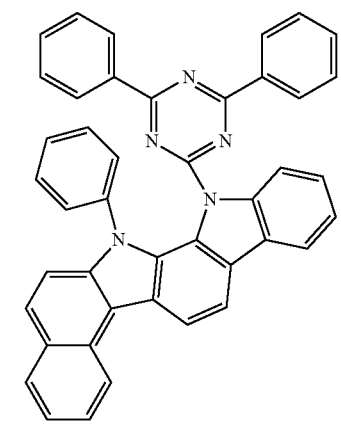
505
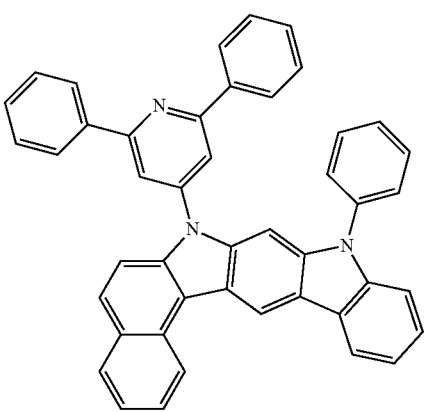
506

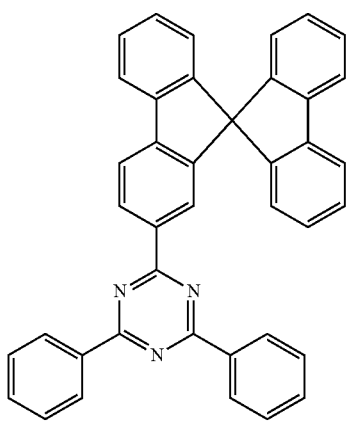

507

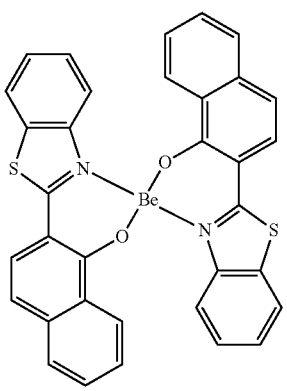

508

In some embodiments, an anthracene-based compound represented by Formula 400 below may be used as the host:

<Formula 400>

Ar$_{114}$—(Ar$_{112}$)$_h$—[core]—(Ar$_{111}$)$_g$—Ar$_{113}$
with (Ar$_{115}$)$_i$ and (Ar$_{116}$)$_j$ substituents wherein, in Formula 400, Ar$_{111}$ and Ar$_{112}$ may each independently be a substituted or unsubstituted C$_5$-C$_{60}$ arylene group; Ar$_{113}$ to Ar$_{116}$ may each independently be a substituted or unsubstituted C1-C10 alkyl group or a substituted or unsubstituted C$_5$-C$_{60}$ aryl group; and g, h, i and j may each independently be an integer from 0 to 4.

For example, Ar$_{111}$ and Ar$_{112}$ in Formula 400 may each independently be selected from a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, and an anthryl group, but is not limited thereto.

g, h, i, and j in Formula 400 may each independently be 0, 1, or 2.

Ar$_{113}$ to Ar$_{116}$ in Formula 400 may each independently be selected from a C$_1$-C$_{10}$ alkyl group substituted with at least one of a phenyl group, a naphthyl group, and an anthryl group;

a phenyl group; a naphthyl group; an anthryl group; a pyrenyl group; a phenanthrenyl group; a fluorenyl group;

a phenyl group, a naphthyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a phenyl group, a naphthyl group, an anthryl group, a pyrenyl group, a phenanthrenyl group, and a fluorenyl group; and

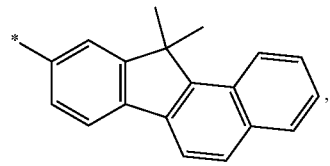 [SMILES: *c1ccc2c(c1)C(C)(C)c1c-2ccc2ccccc12]

but is not limited thereto.

For example, the anthracene-based compound represented by Formula 400 above may be one of the following compounds represented by Formulas below, but is not limited thereto:

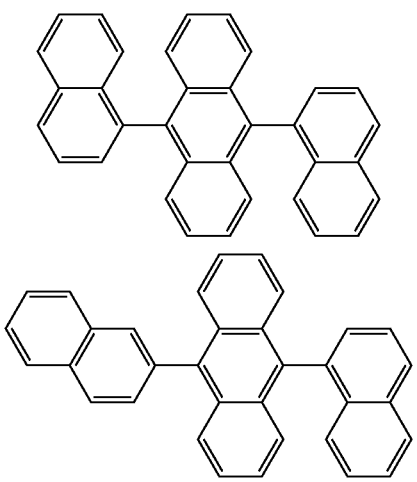

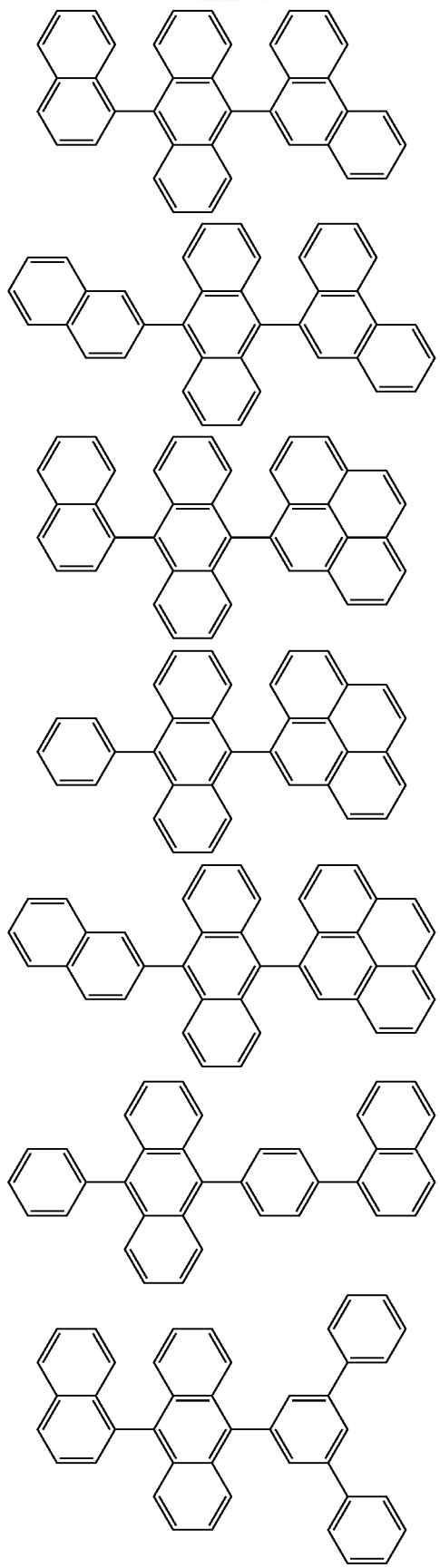
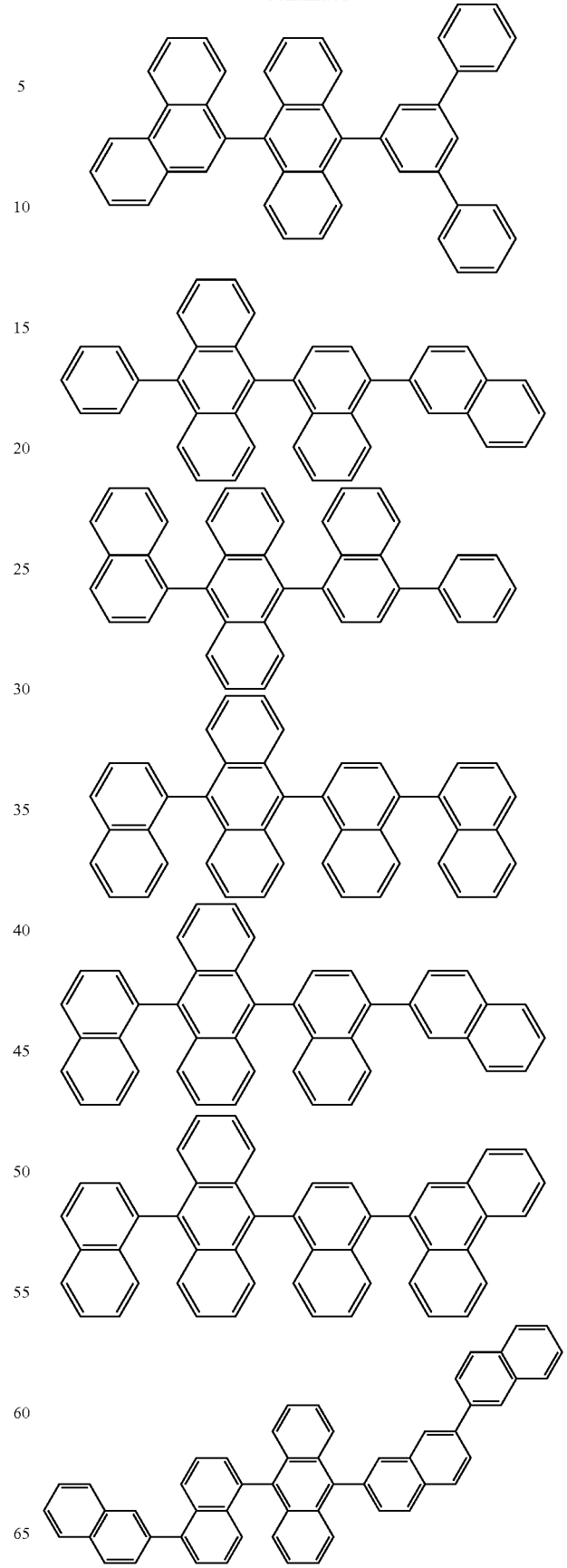

41
-continued
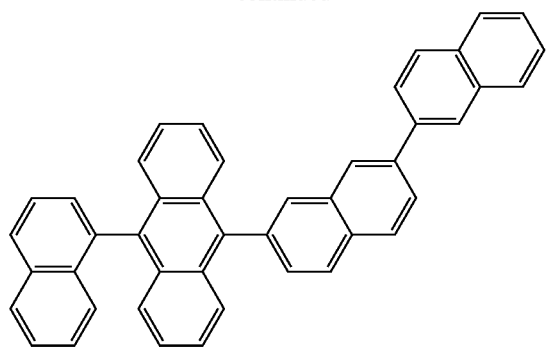
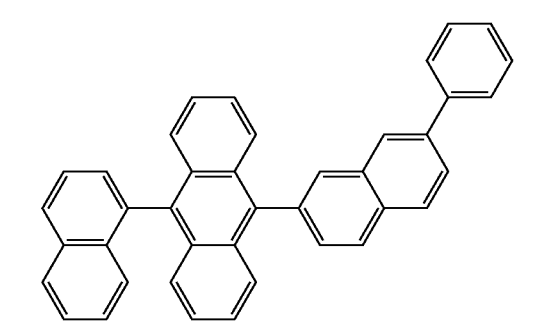
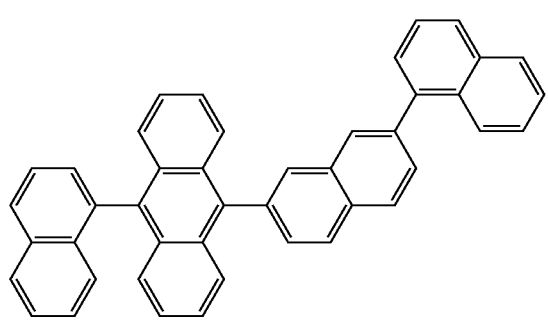
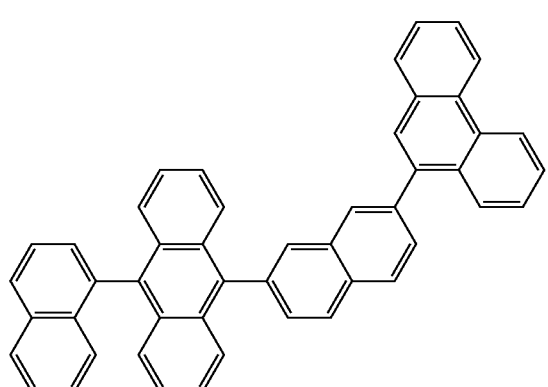
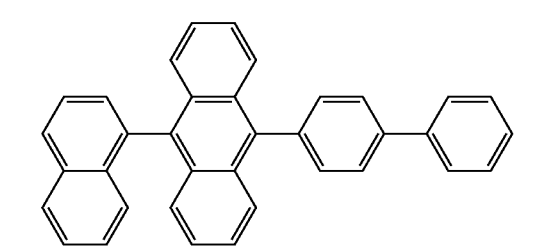
42
-continued
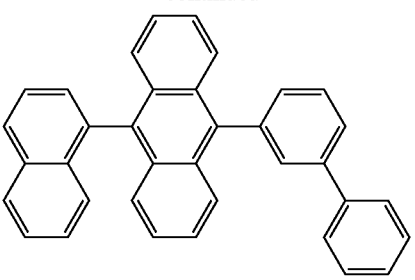
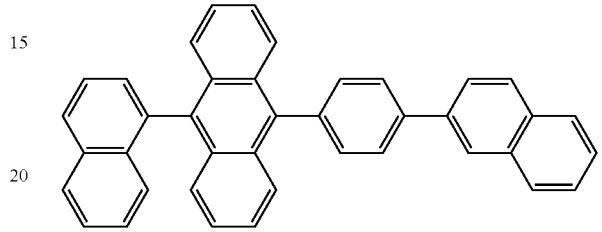
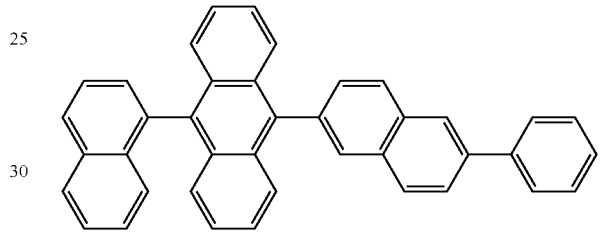
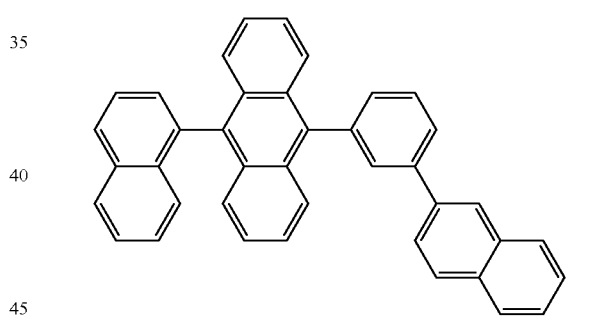
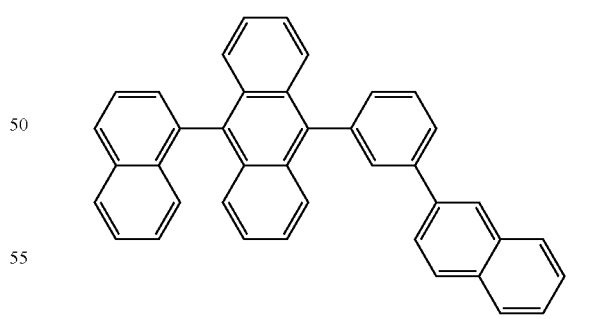
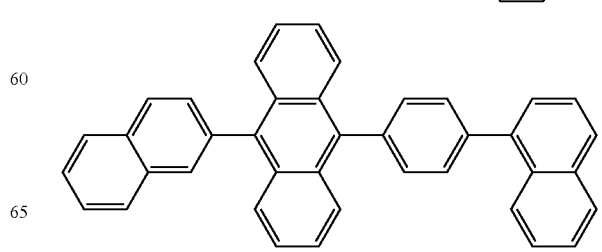

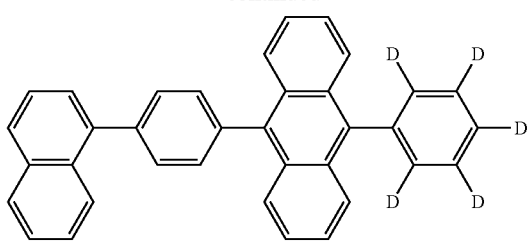
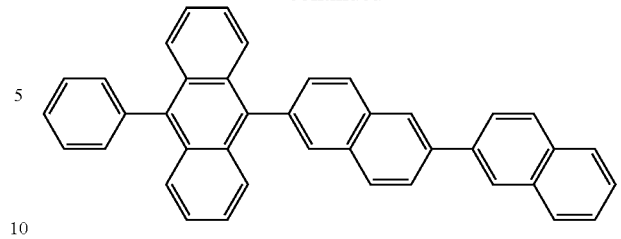
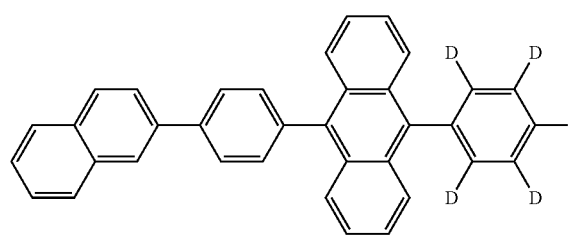
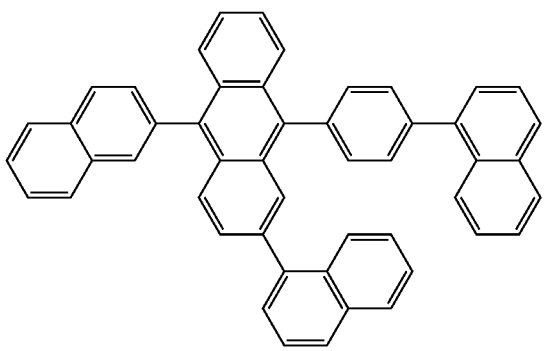
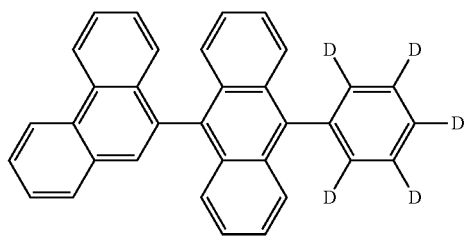
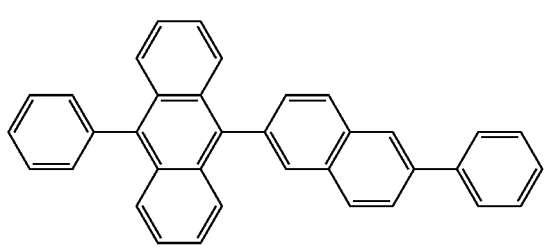
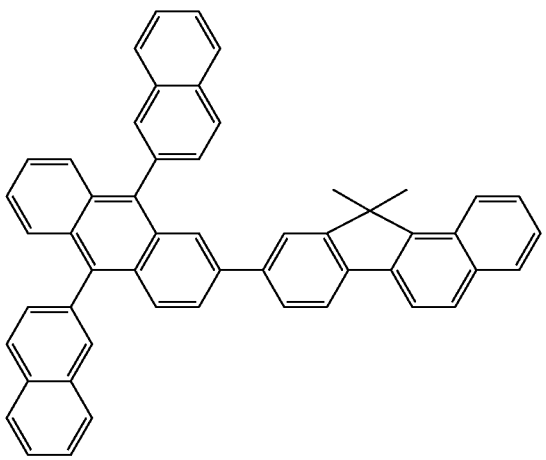

-continued

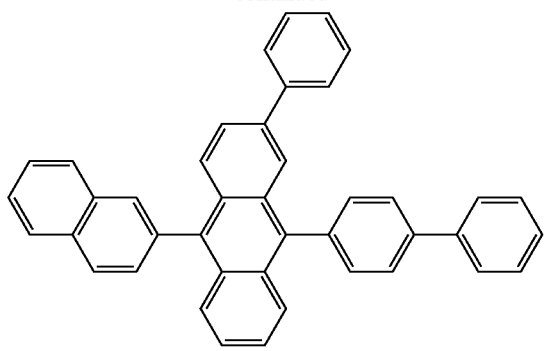

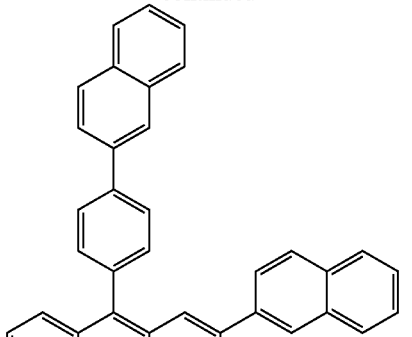

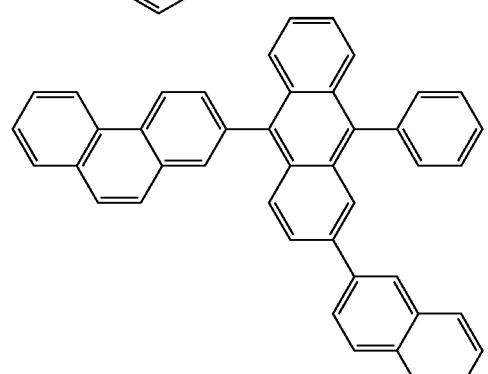

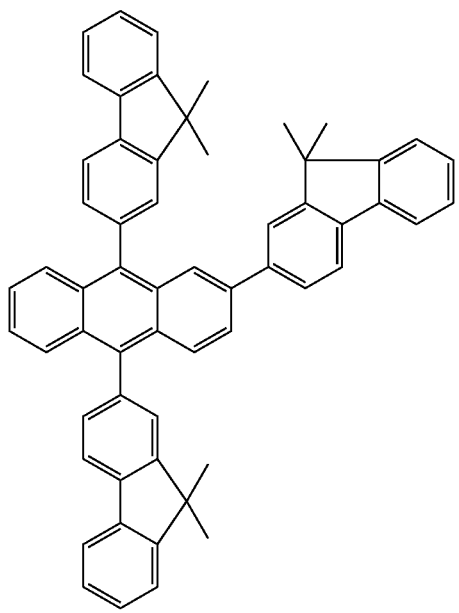

In some embodiments, an anthracene-based compound represented by Formula 401 below may be used as the host:

<Formula 401>

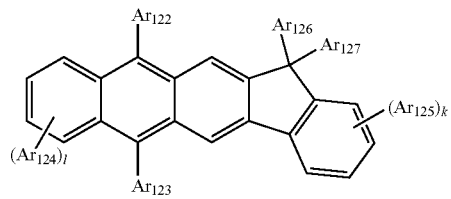

$Ar_{122}$ to $Ar_{125}$ in Formula 401 may be defined as described above with respect to $Ar_{113}$ in Formula 400, and thus detailed descriptions thereof will not be repeated here.

$Ar_{126}$ and $Ar_{127}$ in Formula 401 may each independently be a $C_1$-$C_{10}$ alkyl group (i.e., a methyl group, an ethyl group, or a propyl group).

k and l in Formula 401 may each independently be an integer from 0 to 4. For example, k and l may be 0, 1, or 2.

In some embodiments, the anthracene-based compound represented by Formula 401 may be one of the following compounds represented by Formulas below, but is not limited thereto:

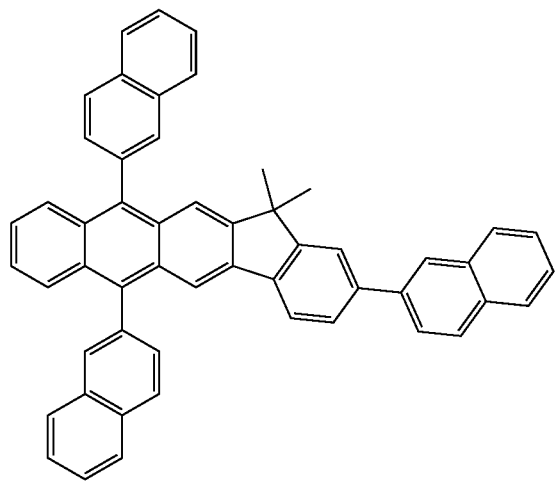
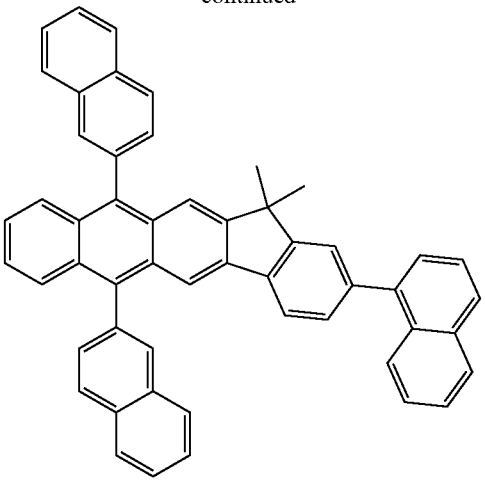
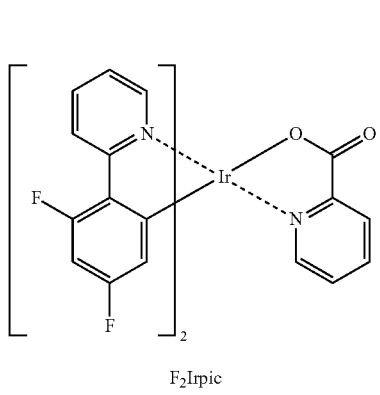

When the OLED is a full color OLED, the EML may be patterned into a red EML, a green EML, and a blue EML.

At least one the red EML, the green EML, and the blue EML may include one of the following dopants below (ppy=phenylpyridine)

Examples of the blue dopant are the following compounds represented by Formulas below, but are not limited thereto:

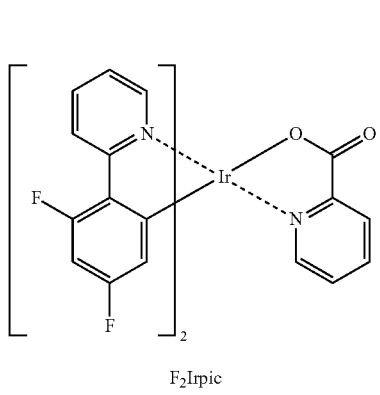
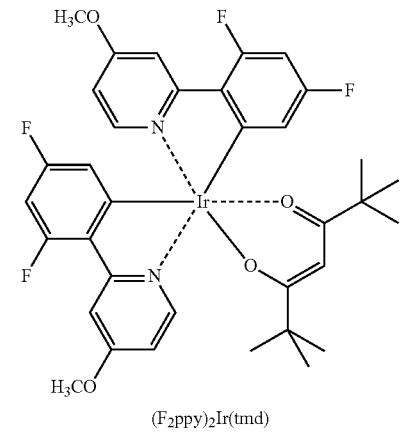
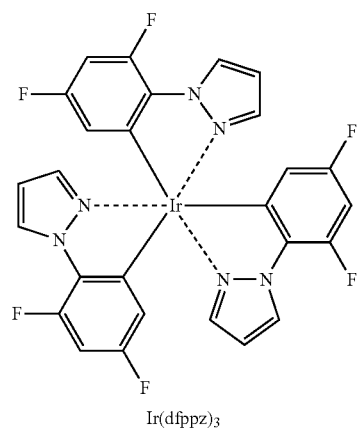

F$_2$Irpic     (F$_2$ppy)$_2$Ir(tmd)     Ir(dfppz)$_3$

-continued
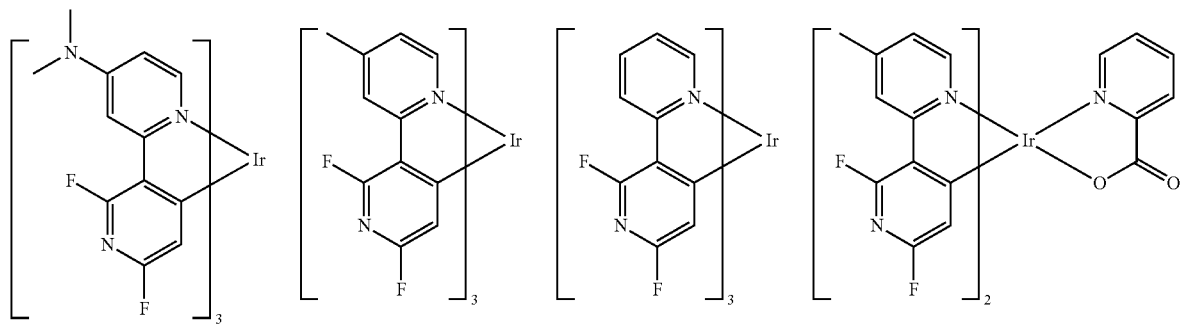
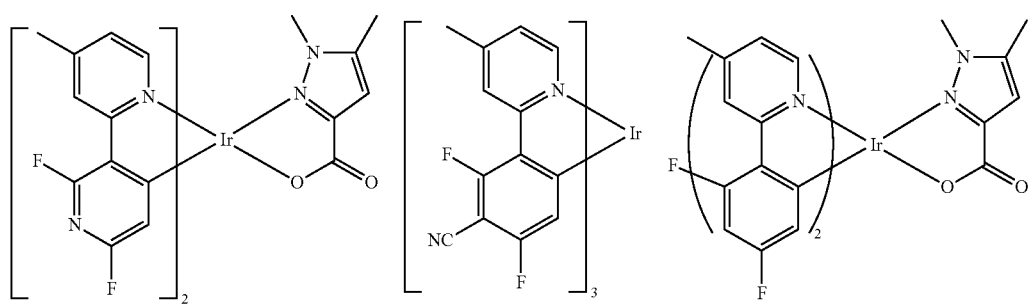
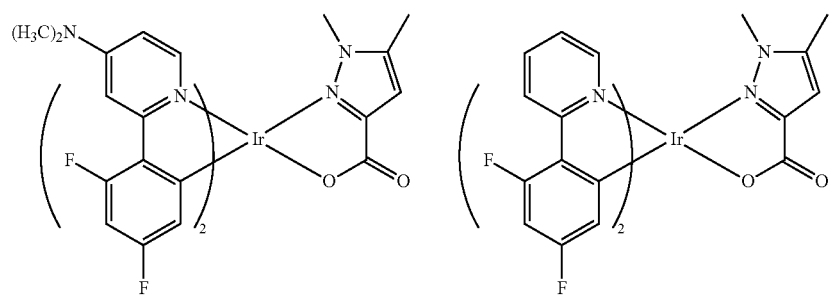
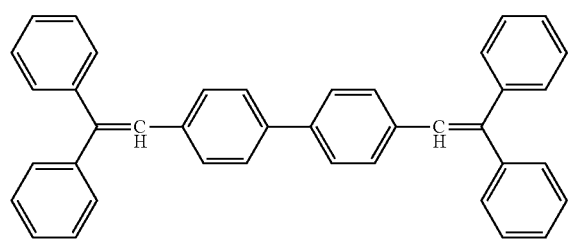
DPVBi
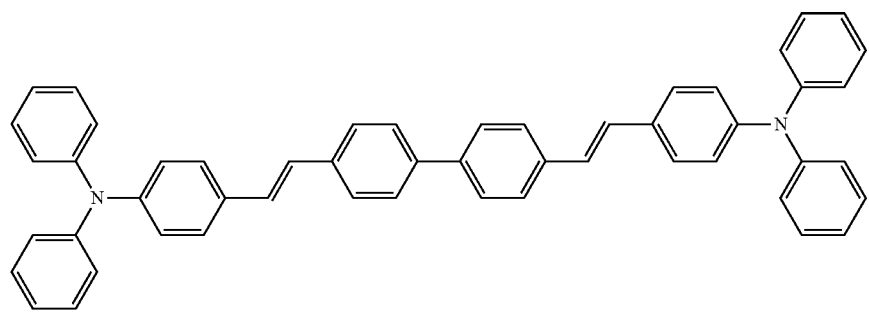
DPAVBi

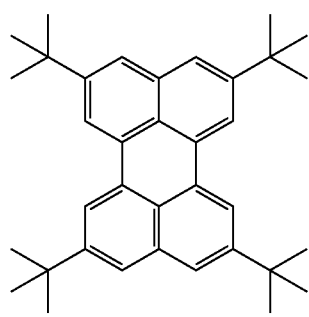
TBPe
Examples of the red dopant are the following compounds represented by Formulas below, but are not limited thereto:
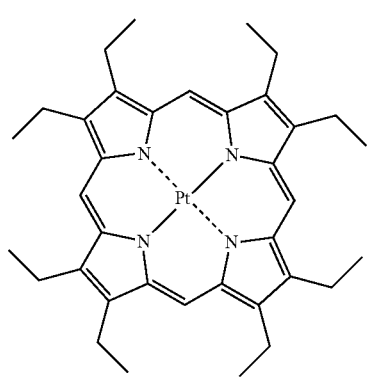
PtOEP
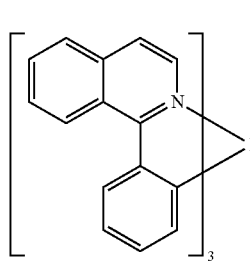
Ir(piq)₃
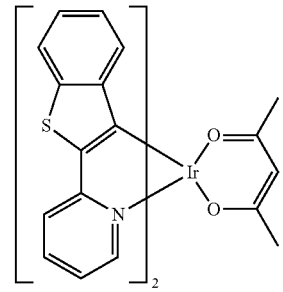
Btp₂Ir(acac)
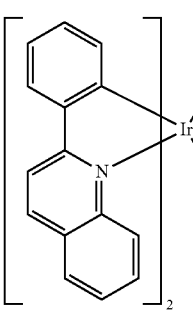
Ir(pq)₂(acac)          Ir(2-phq)₃
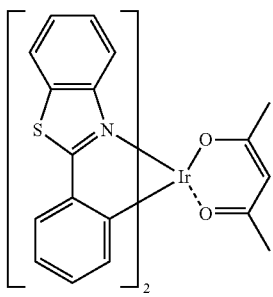
Ir(BT)₂(acac)
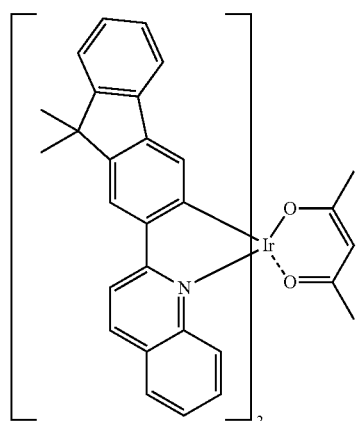
Ir(flq)₂(acac)

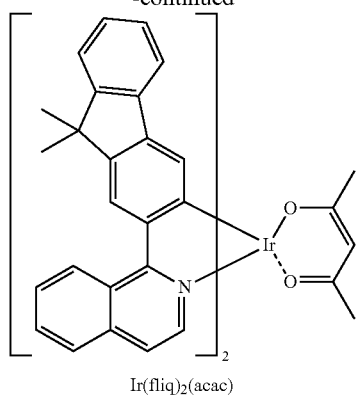
Ir(fliq)₂(acac)
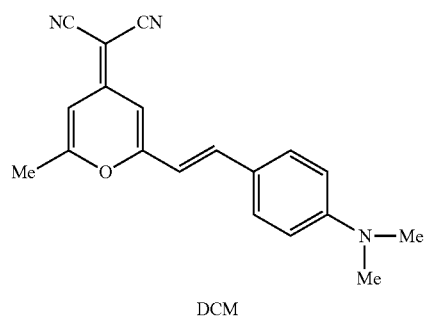
DCM
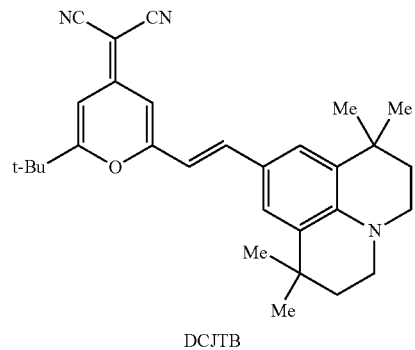
DCJTB
Examples of the green dopant are the following compounds represented by Formulas below, but are not limited thereto:
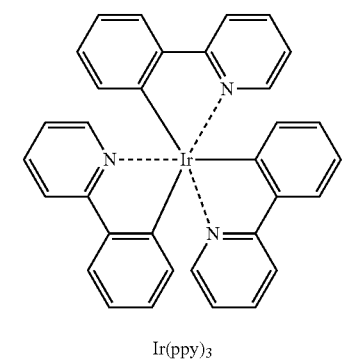
Ir(ppy)₃
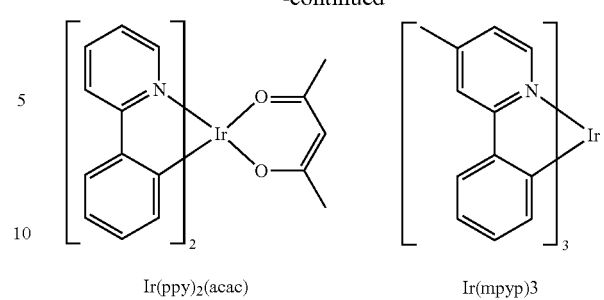
Ir(ppy)₂(acac)　　　　Ir(mpyp)₃
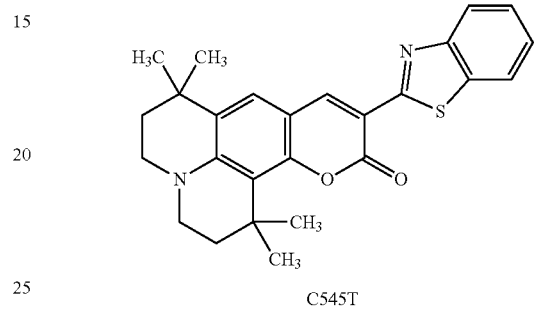
C545T
Examples of dopants that may be used in the EML are Pd complexes or Pt-complexes represented by Formulas below, but are not limited thereto:
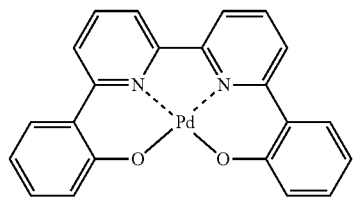
D1
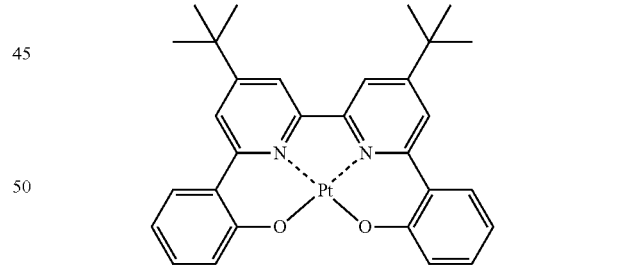
D2
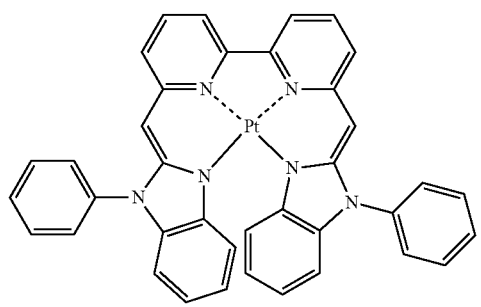
D3

-continued
D4
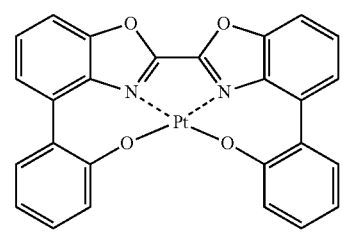
D5
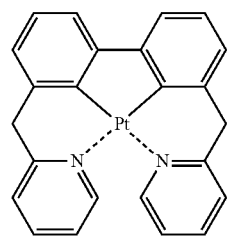
D6
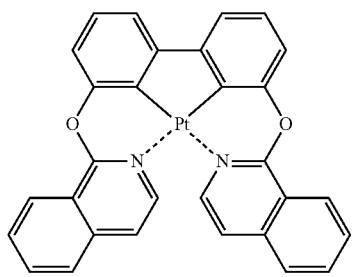
D7
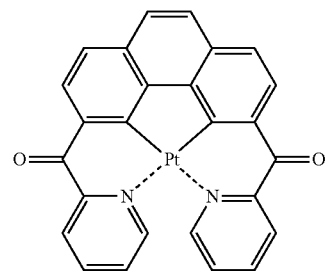
D8
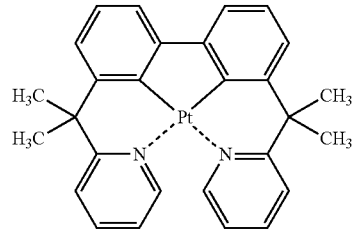
D9
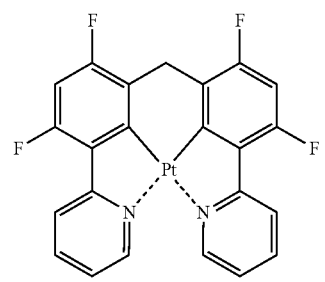
-continued
D10
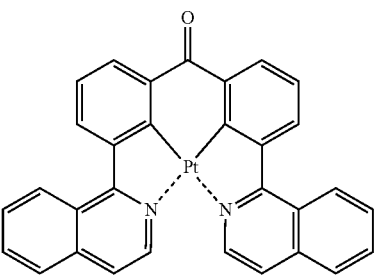
D11
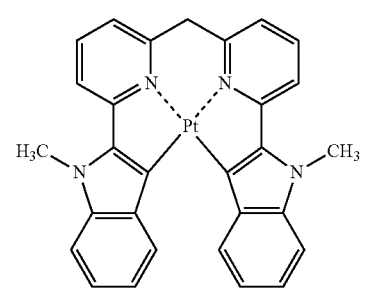
D12
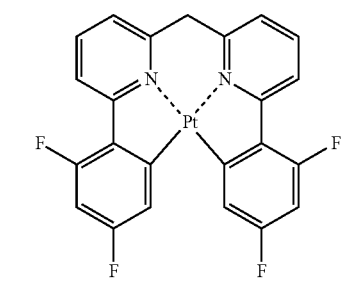
D13
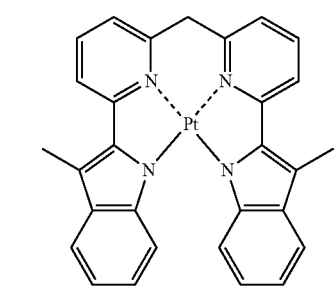
D14
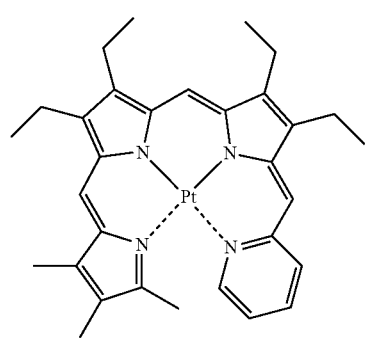

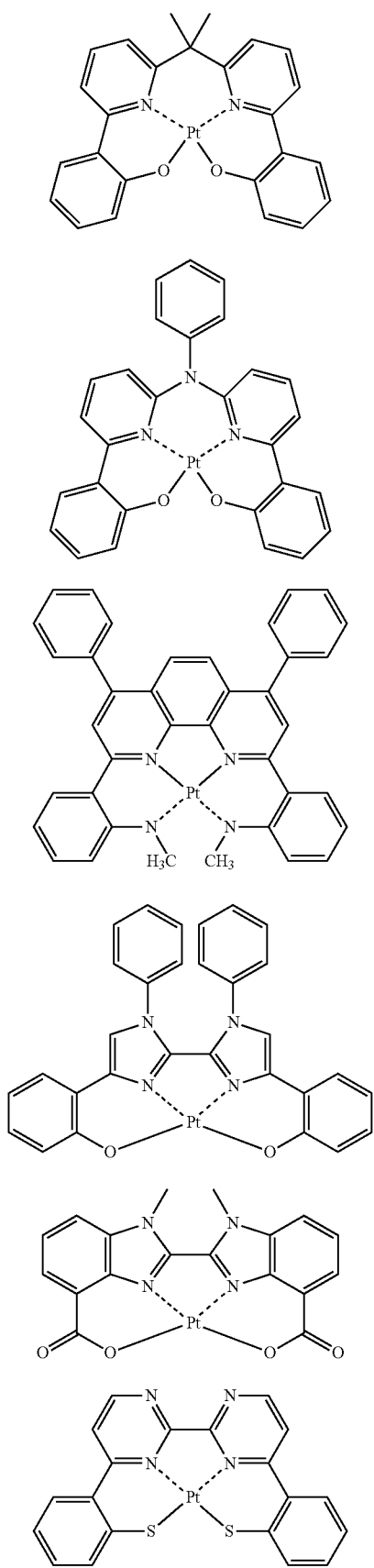
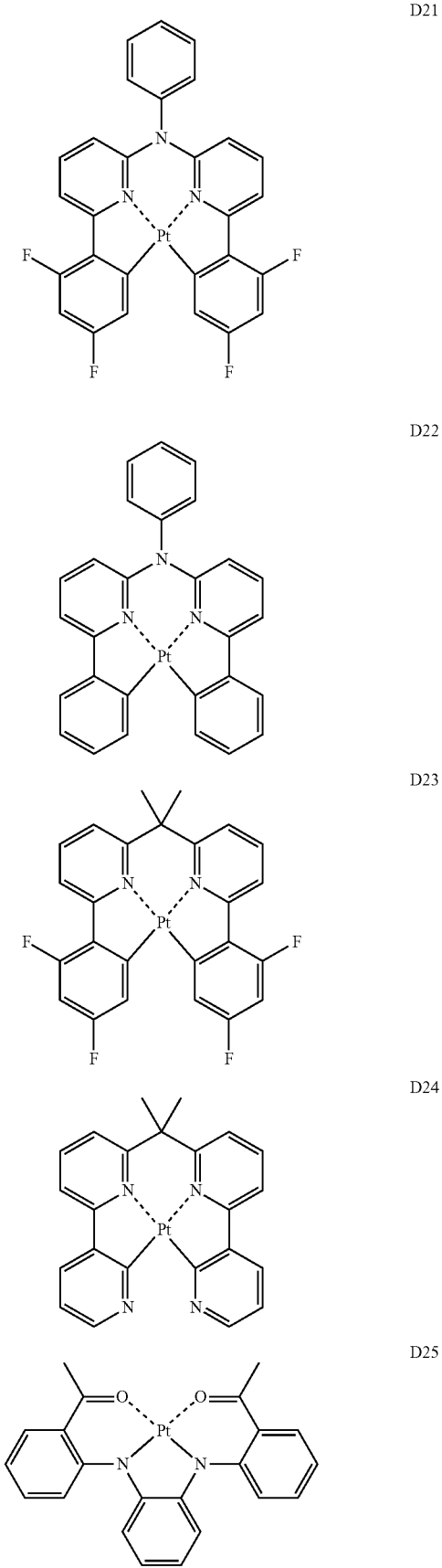

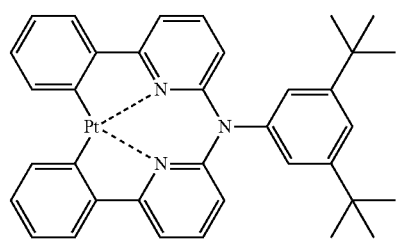
D26
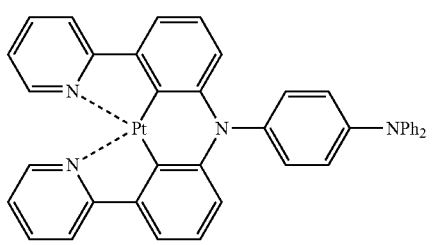
D32
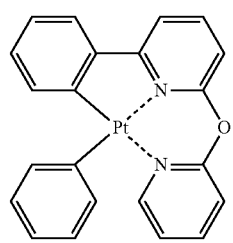
D27
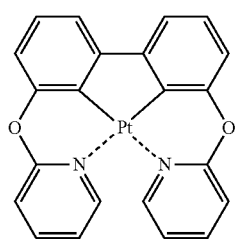
D33
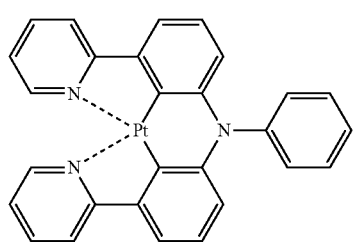
D28
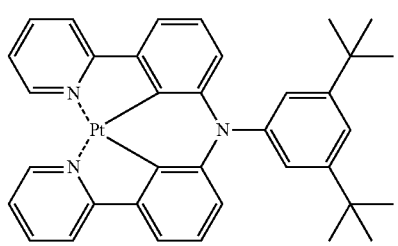
D29
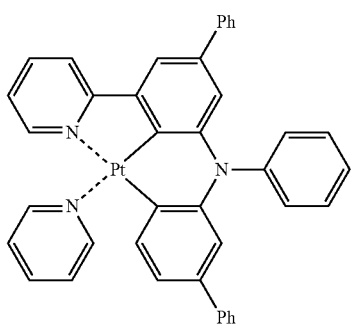
D34
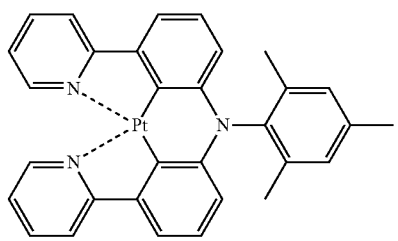
D30
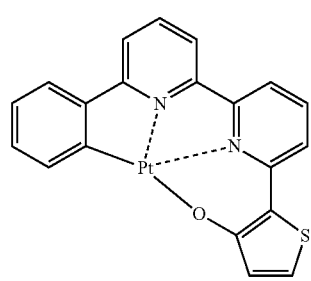
D35
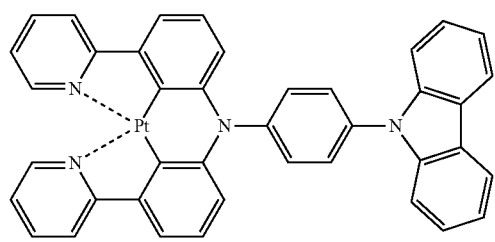
D31
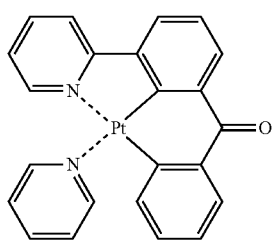
D36

-continued
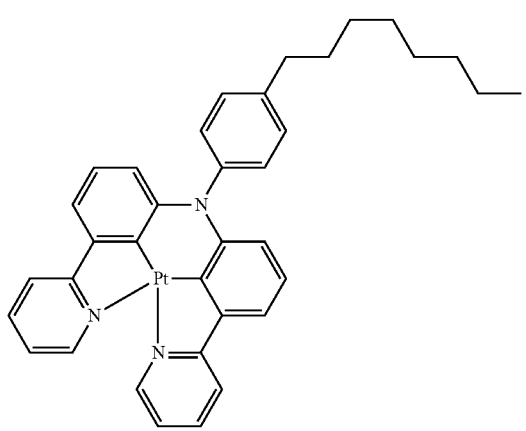
D37
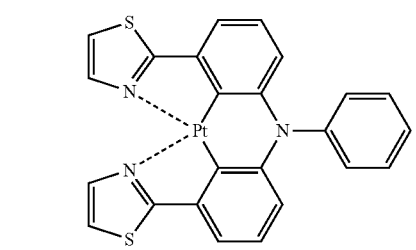
D38
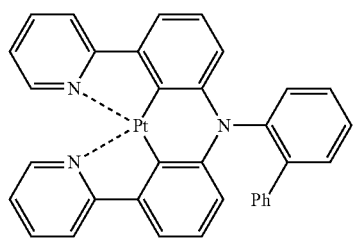
D39
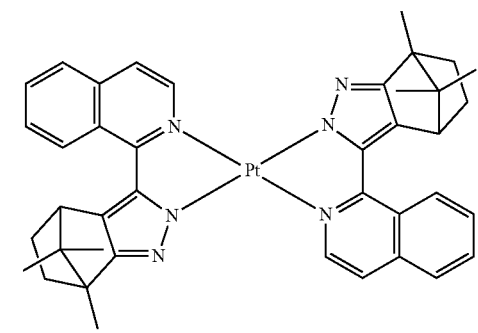
D40
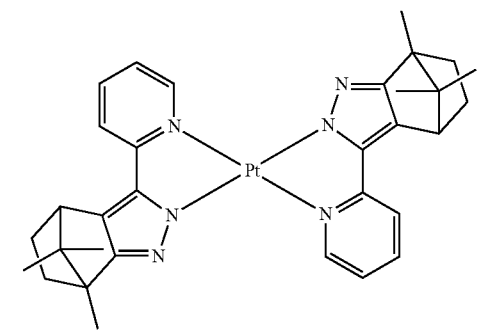
D41
-continued
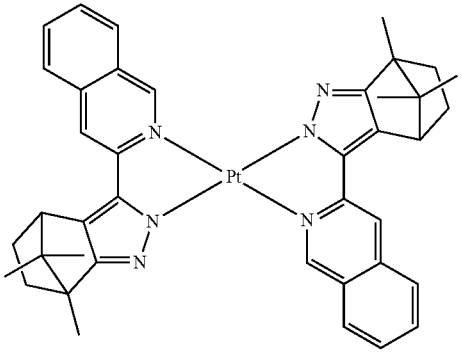
D42
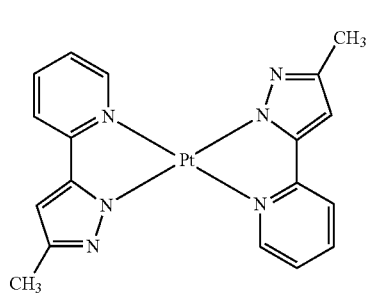
D43
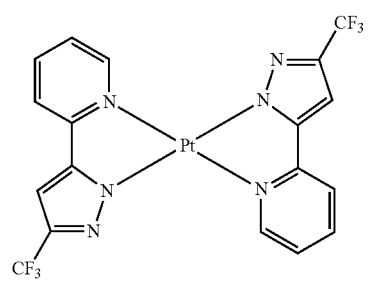
D44
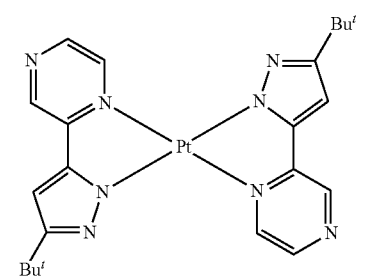
D45
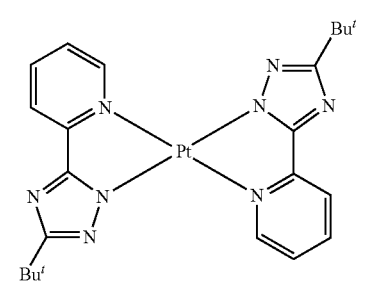
D46

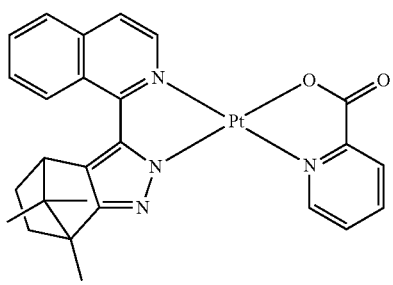

D47

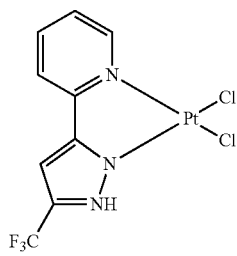

D48

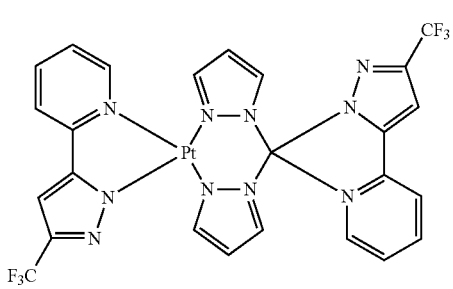

D49

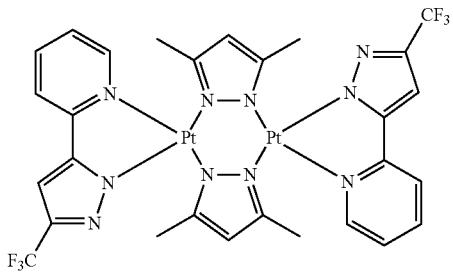

D50

Examples of dopants that may be used in the EML are Os-complexes represented by Formulas below, but are not limited thereto:

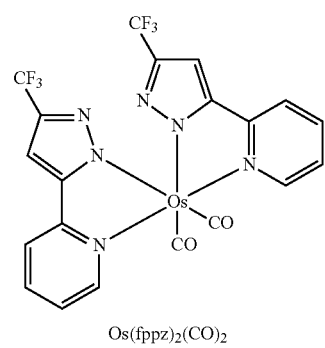

Os(fppz)$_2$(CO)$_2$

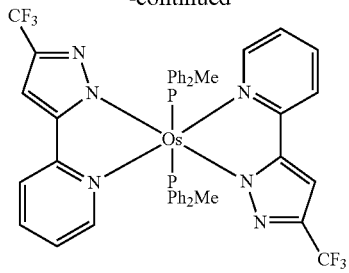

Os(fppz)$_2$(PPh$_2$Me)$_2$

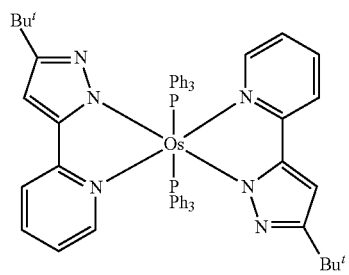

Os(fppz)$_2$(PPh$_3$)$_2$

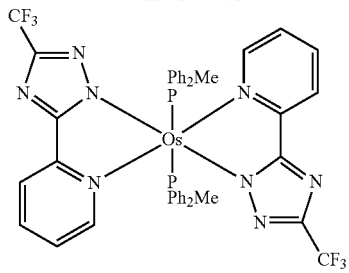

Os(fptz)$_2$(PPh$_2$Me)$_2$

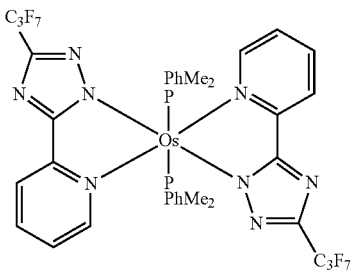

Os(hptz)$_2$(PhMe$_2$)$_2$

When the EML includes a host and a dopant, an amount of the dopant may be in a range from about 0.01 to about 15 parts by weight based on 100 parts by weight of the host, but is not limited thereto.

A thickness of the EML may be in a range from about 100 Å to about 1,000 Å, for example, from about 200 Å to about 600 Å. When the thickness of the EML is within these ranges, the EML may have good light-emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, although the deposition and coating conditions may vary depending on a compound that is used to form the ETL. A material for forming the ETL may be a suitable material that can stably transport electrons injected from an electron-injecting electrode (cathode). Examples of the materials for forming the ETL are a quinoline derivative such as tris(8-quinolinolate)aluminum (Alq3), TAZ, BAlq, beryllium bis(benzoquinolin-10-olate) (Bebq$_2$), 9,10-di (naphthalene-2-yl)anthracene (ADN), Compound 201, and Compound 202, but are not limited thereto:

<Compound 201>

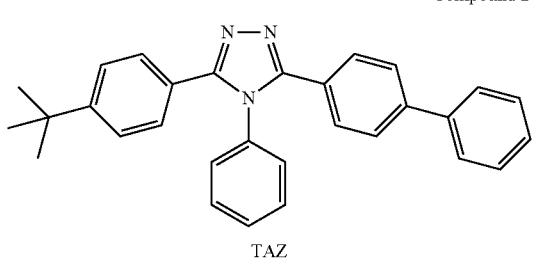

TAZ

<Compound 202>

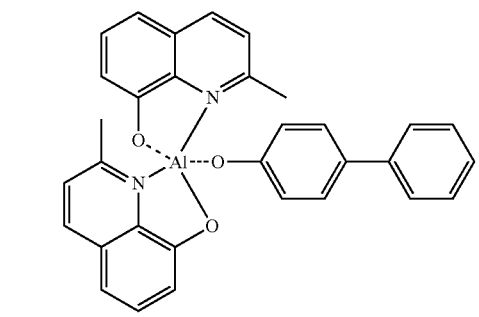

BAlq

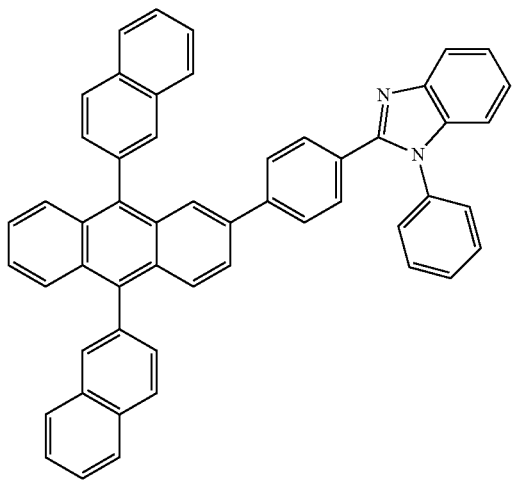

-continued

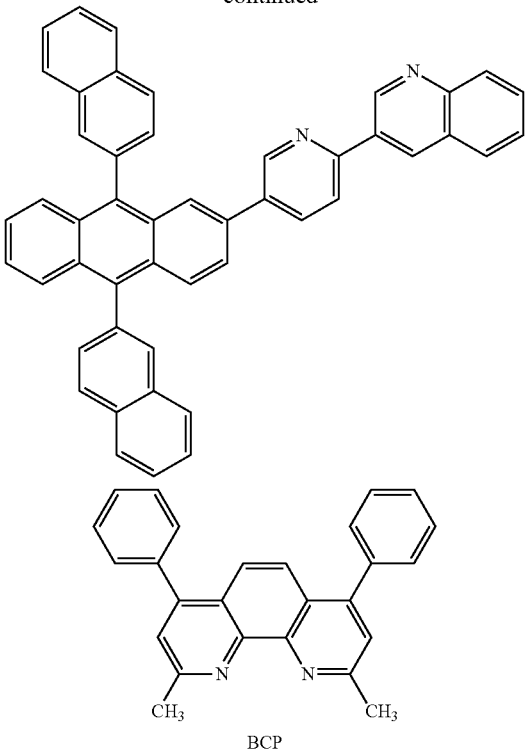

BCP

A thickness of the ETL may be in a range from about 100 Å to about 1,000 Å, for example, from about 150 Å to about 500 Å. When the thickness of the ETL is within these ranges, the ETL may have a satisfactory electron transporting ability without a substantial increase in driving voltage.

In some embodiments, the ETL may further include a metal-containing material, in addition to a general electron transporting organic compound.

The metal-containing material may include a lithium (Li) complex. Non-limiting examples of the Li complex are lithium quinolate (LiQ) and Compound 203 below:

<Compound 203>

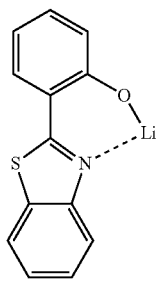

Then, an EIL, which facilitates injection of electrons from the cathode, may be formed on the ETL. A suitable electron-injecting material may be used to form the EIL.

Examples of materials for forming the EIL are LiF, NaCl, CsF, Li$_2$O, and BaO. Deposition conditions of the EIL may be similar to those for the formation of the HIL, although the conditions may vary depending on a material that is used to form the EIL.

A thickness of the EIL may be in a range from about 1 Å to about 100 Å, for example, from about 3 Å to about 90 Å.

When the thickness of the EIL is within these ranges, the EIL may have satisfactory electron injection ability without a substantial increase in driving voltage.

A second electrode is disposed on the organic layer. The second electrode may be a cathode that is an electron injection electrode. Here, material for forming the second electrode may be a metal, an alloy, and an electro-conductive compound, which have a low work function, or a mixture thereof. In this regard, the second electrode may be formed of lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

An OLED according to an example embodiment has already been described above with reference to FIG. 1, but is not limited to the structure illustrated in FIG. 1.

In addition, when the EML is formed using a phosphorescent dopant, to prevent diffusion of triplet excitons or holes toward the ETL, a hole blocking layer (HBL) may be formed between the HTL and the EML or between the H-functional layer and the EML by a method such as, for example, vacuum deposition, spin coating, casting, LB, or the like. When the HBL is formed using vacuum deposition or spin coating, the deposition and coating conditions may be similar to those for the formation of the HIL, although the conditions for deposition and coating may vary depending on the material that is used to form the HBL. A suitable general hole-blocking material may be used. Non-limiting examples of hole-blocking materials are oxadiazole derivatives, triazole derivatives, and phenanthroline derivatives. For example, BCP illustrated below may be used as a material for the HBL.

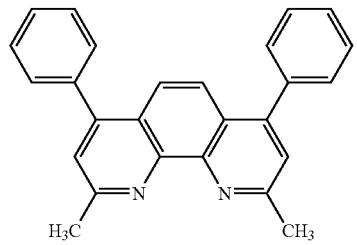

BCP

A thickness of the HBL may be in a range from about 20 Å to about 1,000 Å, for example, from about 30 Å to about 300 Å. When the thickness of the HBL is within these ranges, the HBL may have an improved hole blocking ability without a substantial increase in driving voltage.

The OLED according to an example embodiment may be provided in various types of flat panel display devices such as passive matrix OLED devices and active matrix OLED devices. When the OLED is provided in an active matrix OLED, the first electrode on the substrate, which acts as a pixel electrode, may be electrically connected to a source electrode or a drain electrode of a thin-film transistor (TFT). In addition, the OLED may be provided in a flat panel display device having double-sided screens.

In some embodiments the organic layer of the organic light-emitting device may be formed of the compound of Formula 1 by using a deposition method or may be formed using a wet process of coating a solution of the compound of Formula 1.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

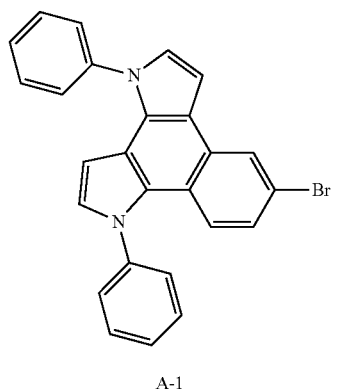

A-1

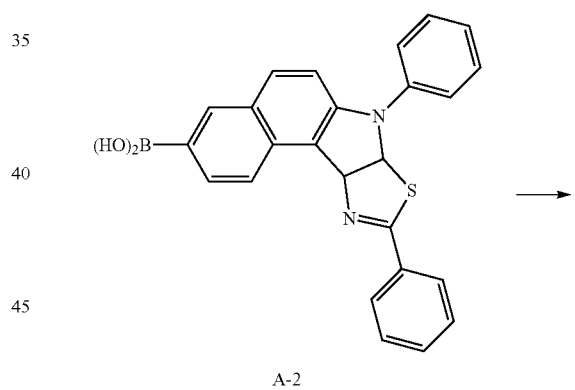

A-2

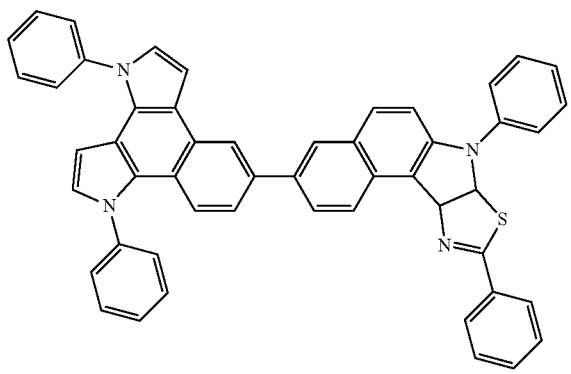

1

10 g (1 eq, 0.0229 mol) of A-1 and 10.6 g (1.1 eq, 0.0252 mol) of A-2 were each added in a flask, and then dissolved in 600 ml of toluene. 0.529 g (0.02 eq, 0.000458 mmol) of Pd(PPh$_3$)$_4$ and 70 ml of K$_2$CO$_3$ 2 M solution were each added thereto, and then stirred for 12 hours. After completion of the reaction, the reaction solution was filtered through Celite. Then, 13.8 g (Yield=82.3%) of the final compound 1 was obtained by column chromatography.

Elemental Analysis for C51H34N4S: calcd: C, 83.35; H, 4.66; N, 7.62; S, 4.36

HRMS for C51H34N4S [M]+: calcd 734.25, found 734.

Synthesis Example 2

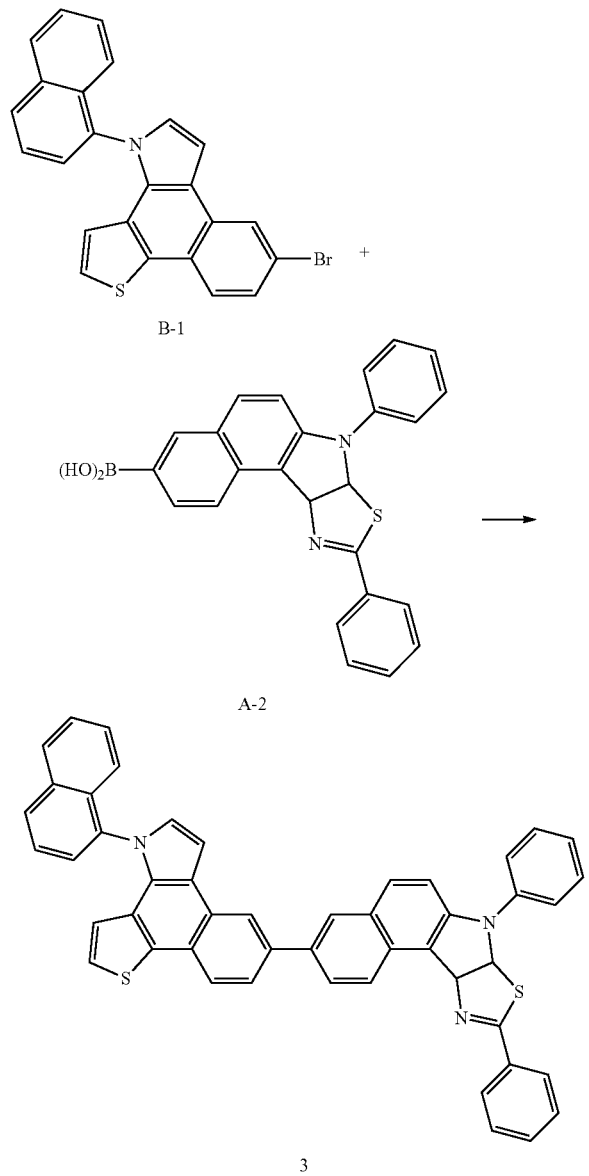

3

10 g (1 eq, 0.0234 mol) of B-1 and 10.6 g (1.1 eq, 0.0257 mol) of A-2 were each added in a flask, and then dissolved in 600 ml of toluene. 0.514 g (0.02 eq, 0.000468 mmol) of Pd(PPh$_3$)$_4$ and 70 ml of K$_2$CO$_3$ 2 M solution were each added thereto, and then stirred for 12 hours. After completion of the reaction, the reaction solution was filtered through Celite. then, 12.5 g (Yield=73.8%) of the final compound 3 was obtained by column chromatography.

Elemental Analysis for C49H31N3S2: calcd: C, 81.07; H, 4.30; N, 5.79; S, 8.83

HRMS for C49H31N3S2 [M]+: calcd 725.2, found 725.

Synthesis Example 3

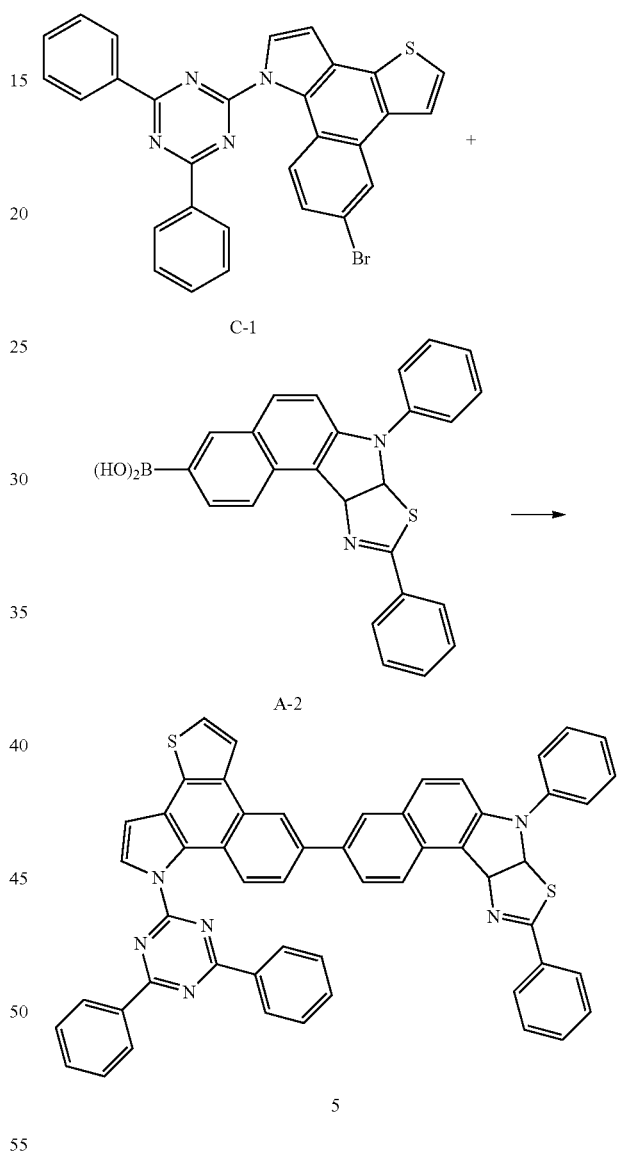

5

10 g (1 eq, 0.0187 mol) of C-1 and 8.7 g (1.1 eq, 0.0206 mol) of A-2 were each added in a flask, and then dissolved in 450 ml of toluene. 0.514 g (0.02 eq, 0.000468 mmol) of Pd(PPh$_3$)$_4$ and 40 ml of K$_2$CO$_3$ 2 M solution were each added thereto, and then stirred for 12 hours. After completion of the reaction the reaction solution was filtered through Celite. Then, 10.7 g (Yield=69.2%) of the final compound 5 was obtained by column chromatography.

Elemental Analysis for C54H34N6S2: calcd: C, 78.05; H, 4.12; N, 10.11; S, 7.72

HRMS for C54H34N6S2 [M]+: calcd 830.23, found 830.

Synthesis Example 4

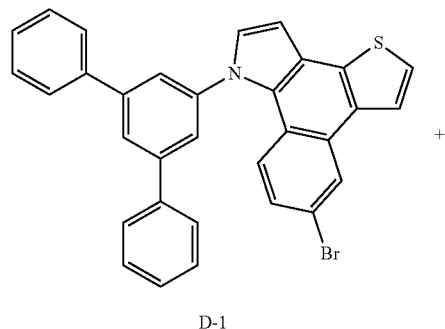

D-1

+

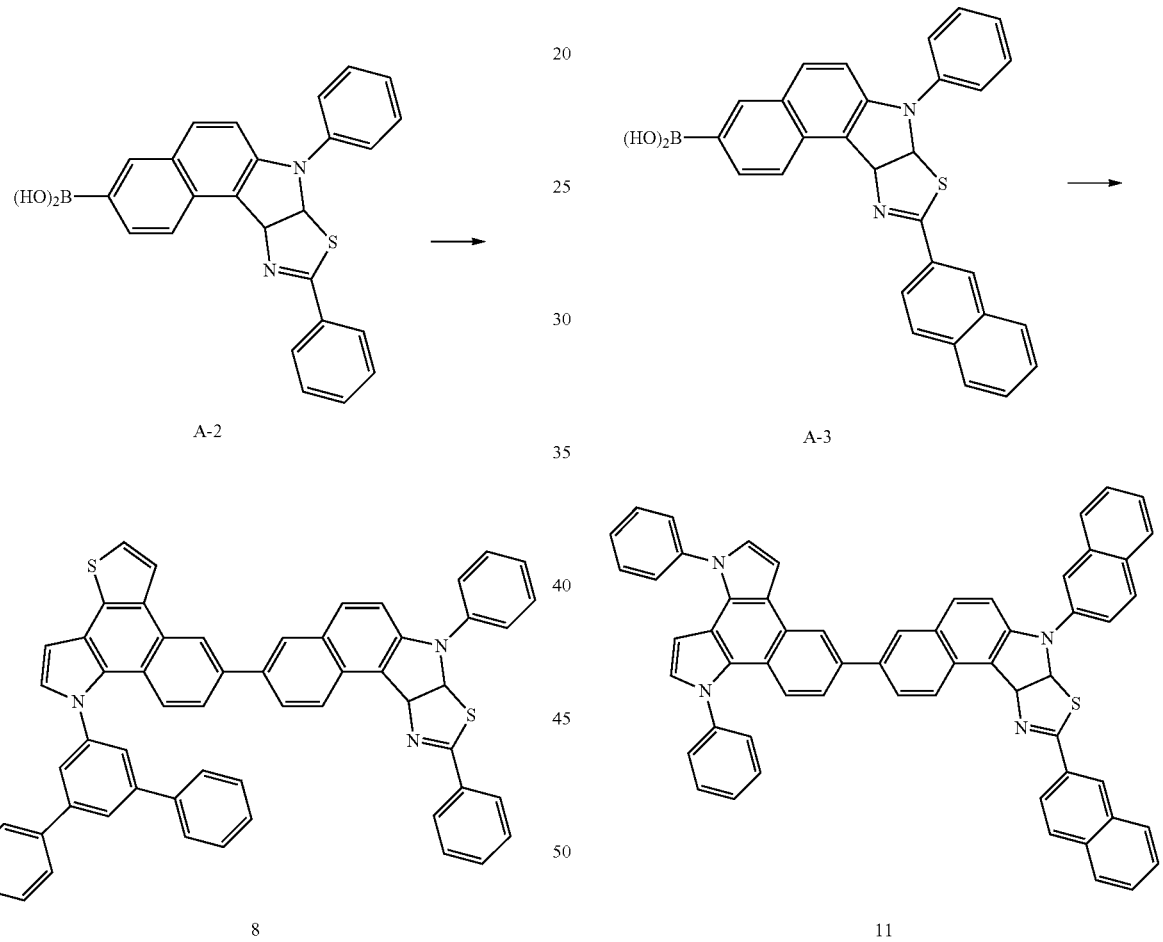

10 g (1 eq, 0.0189 mol) of D-1 and 8.7 g (1.1 eq, 0.0207 mol) of A-2 were each added in a flask, and then dissolved in 550 ml of toluene. 0.5 g (0.02 eq, 0.000415 mmol) of Pd(PPh$_3$)$_4$ and 55 ml of K$_2$CO$_3$ 2 M solution were each added thereto, and then stirred for 12 hours. After completion of the reaction, the reaction solution was filtered through Celite. Then, 11.08 g (Yield=70.9%) of the final compound 8 was obtained by column chromatography.

Elemental Analysis for C57H37N3S2: calcd: C, 82.68; H, 4.50; N, 5.07; S, 7.74

HRMS for C57H37N3S2 [M]+: calcd 827.24, found 827.

Synthesis Example 5

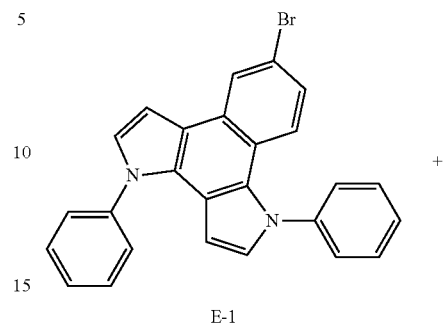

E-1

+

10 g (1 eq, 0.0229 mol) of E-1 and 8.7 g (1.1 eq, 0.0252 mol) of A-3 were each added in a flask, and then dissolved in 500 ml of toluene. 0.529 g (0.02 eq, 0.000458 mmol) of Pd(PPh$_3$)$_4$ and 50 ml of K$_2$CO$_3$ 2 M solution were each added thereto, and then stirred for 12 hours. After completion of the reaction, the reaction solution was filtered through Celite. Then, 12.62 g (Yield=66.1%) of the final compound 11 was obtained by column chromatography.

Elemental Analysis for C59H38N4S: calcd: C, 84.86; H, 4.59; N, 6.71; S, 3.84

HRMS for C59H38N4S [M]+: calcd 834.28, found 834

Synthesis Example 6

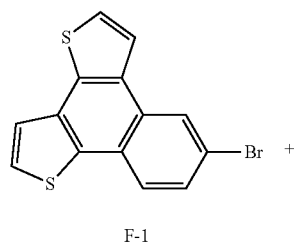

F-1

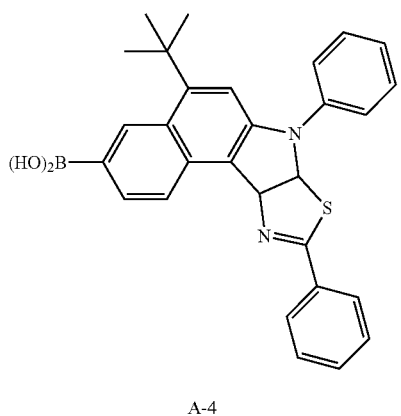

A-4

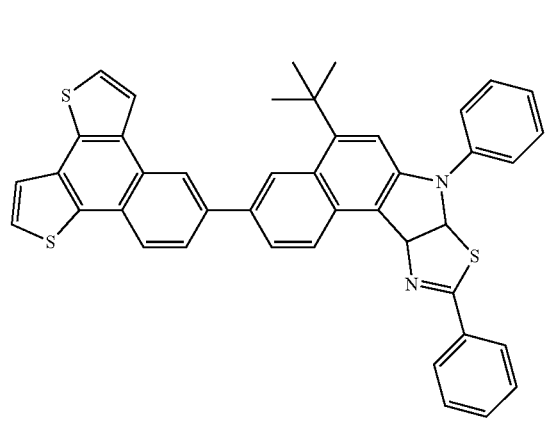

15

10 g (1 eq, 0.0314 mol) of F-1 and 16.54 g (1.1 eq, 0.0345 mol) A-4 were each added in a flask, and then dissolved in 500 ml of toluene. 0.725 g (0.02 eq, 0.000628 mmol) of Pd(PPh$_3$)$_4$ and 50 ml of K$_2$CO$_3$ 2 M solution were each added thereto, and then stirred for 12 hours. After completion of the reaction, the reaction solution was filtered through Celite. Then, 15.9 g (Yield=75.6.1%) of the final compound 15 was obtained by column chromatography.

Elemental Analysis for C43H32N2S3: calcd: C, 76.75; H, 4.79; N, 4.16; S, 14.30

HRMS for C43H32N2S3 [M]+: calcd 672.17, found 672

Synthesis Example 7

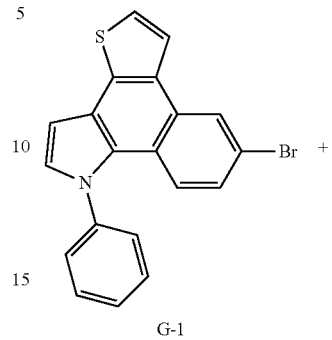

G-1

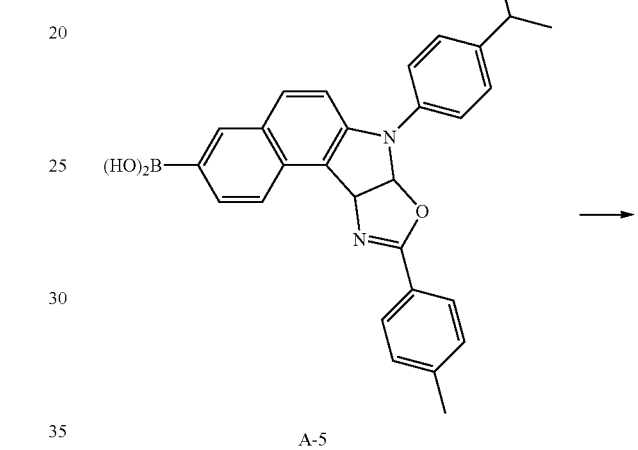

A-5

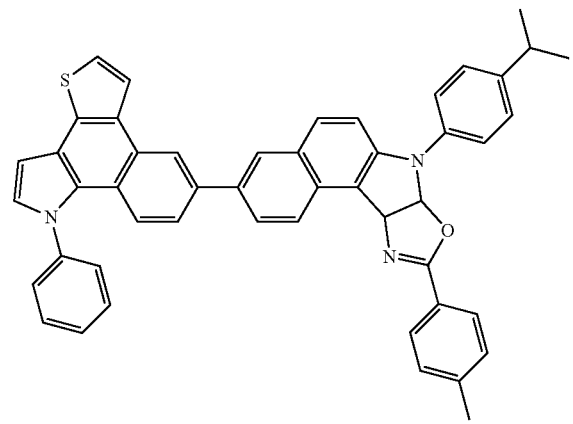

18

10 g (1 eq, 0.0265 mol) of G-1 and 14.3 g (1.1 eq, 0.0291 mol) of A-5 were each added in a flask, and then dissolved in 500 ml of toluene. 0.612 g (0.02 eq, 0.00053 mmol) of Pd(PPh$_3$)$_4$ and 50 ml of K$_2$CO$_3$ 2 M solution were each added thereto, and then stirred for 12 hours. After completion of the reaction, the reaction solution was filtered through Celite. Then, 12.98 g (Yield=71.8%) of the final compound 18 was obtained by column chromatography.

Elemental Analysis for C46H38N2S2: calcd: C, 80.90; H, 5.61; N, 4.10; S, 9.39

FIRMS for C46H38N2S2 [M]+: calcd 682.25, found 682

Synthesis Example 8

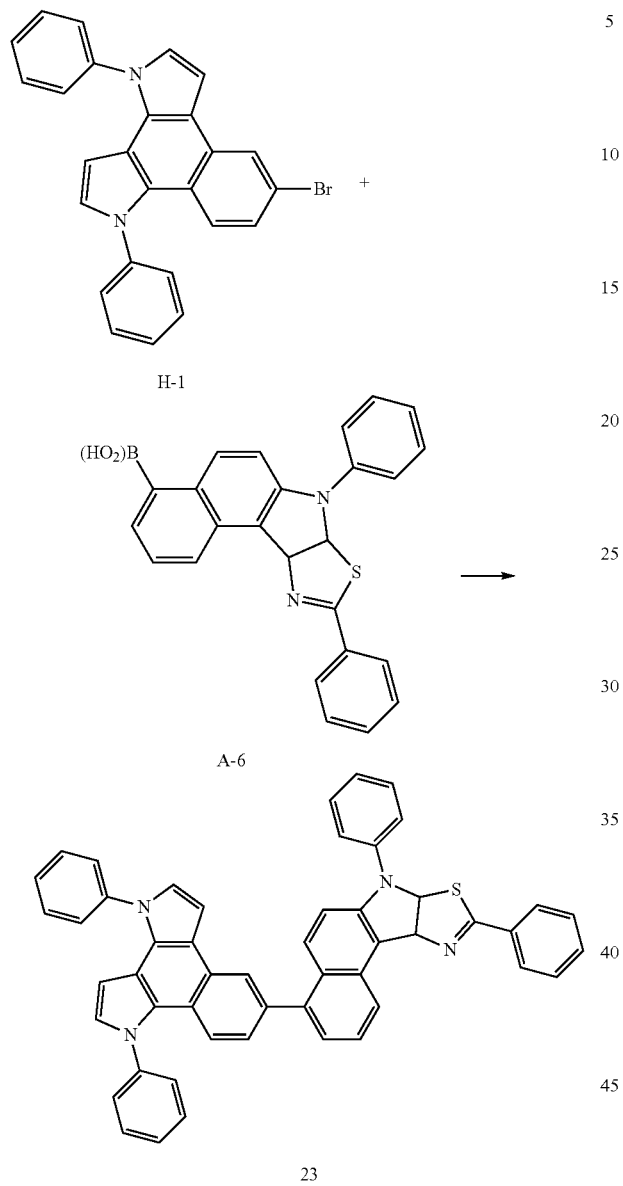

10 g (1 eq, 0.0229 mol) of H-1 and 10.6 g (1.1 eq, 0.0252 mol) of A-6 were each added in a flask, and then dissolved in 500 ml of toluene. 0.529 g (0.02 eq, 0.00045 mmol) of Pd(PPh$_3$)$_4$ and 50 ml of K$_2$CO$_3$ 2 M solution were each added thereto, and then stirred for 12 hours. After completion of the reaction, the reaction solution was filtered through Celite. Then, 11.06 g (Yield=65.8%) of the final compound 23 was obtained by column chromatography.

Elemental Analysis for C51H34N4S: calcd: C, 83.35; H, 4.66; N, 7.62; S, 4.36

HRMS for C51H34N4S [M]+: calcd 734.25 found 734

Example 1

An anode was prepared by cutting a Corning 15 Ω/cm² (500 Å) ITO glass substrate to a size of 50 mm×50 mm×0.5 mm, sonicated in isopropyl alcohol for 10 minutes and in pure water for 10 minutes, and then cleaned by irradiation of ultraviolet rays for 10 minutes, and exposed to ozone. The ITO glass substrate was then loaded onto a vacuum deposition device. 2-TNATA was vacuum deposited on the anode to a thickness of about 600 Å to form an HIL, and 4'-bis[N-(1-naphthyl)-N-phenylamino]biphenyl (hereinafter, NPB) as a hole transporting compound was vacuum-deposited on the HIL to a thickness of about 300 Å.

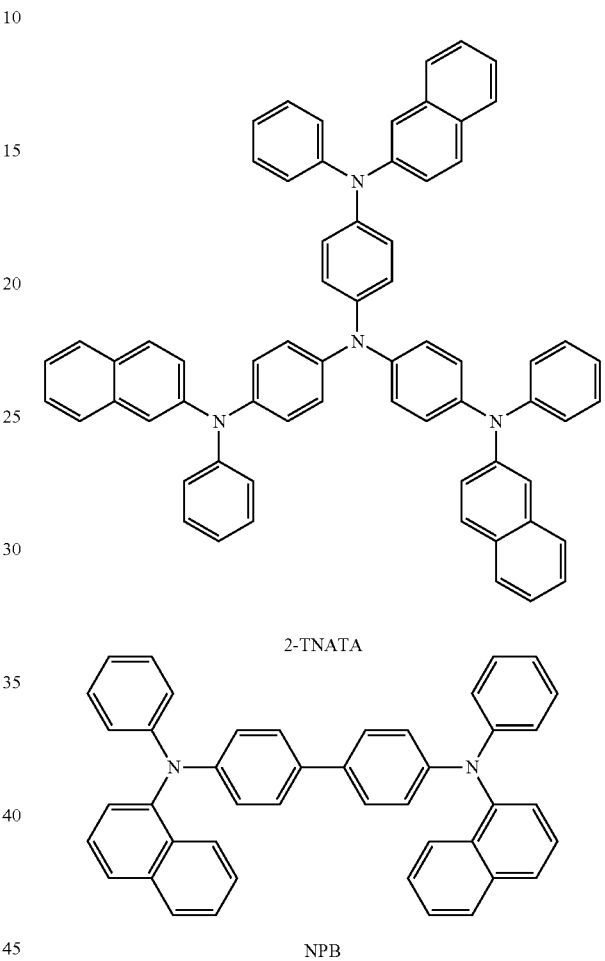

Ir(ppy)$_3$ as a phosphorescent dopant, and Compound 1 above were co-deposited at a weight ratio of about 13:87 on the HTL to form an EML having a thickness of 300 Å. Next, Alq3 was deposited on the EML to form an ETL to a thickness of about 300 Å. Then, Al was vacuum-deposited on the ETL to form a cathode having a thickness of about 1,200 Å, thereby forming an Al electrode and completing the manufacture of an OLED.

The OLED had high efficiency with a driving voltage of about 3.6 V at a current density of 5.4 mA/cm², a luminosity of 3,500 cd/m², a color coordinate of 0.32 and 0.62 and a luminescent efficiency of 70.5 cd/A.

Example 2

An OLED was manufactured in the same manner as in Example 1, except that Compound 3 was used instead of Compound 1 to form the ETL.

The OLED had high efficiency with a driving voltage of about 4.1 V at a current density of 5.9 mA/cm², a luminosity of 3,500 cd/m², a color coordinate of 0.32 and 0.63 and a luminescent efficiency of 67.9 cd/A.

Example 3

An OLED was manufactured in the same manner as in Example 1, except that Compound 5 was used instead of Compound 1 to form the ETL.

The OLED had high efficiency with a driving voltage of about 4.5 V at a current density of 5.9 mA/cm², a luminosity of 3,500 cd/m², a color coordinate of 0.33 and 0.63 and a luminescent efficiency of 67.7 cd/A.

Example 4

An OLED was manufactured in the same manner as in Example 1, except that Compound 8 was used instead of Compound 1 to form the ETL.

The OLED had high efficiency with a driving voltage of about 3.9 V at a current density of 5.9 mA/cm², a luminosity of 3,500 cd/m², a color coordinate of 0.34 and 0.61 and a luminescent efficiency of 65.3 cd/A.

Example 5

An OLED was manufactured in the same manner as in Example 1, except that Compound 11 was used instead of Compound 1 to form the ETL.

The OLED had high efficiency with a driving voltage of about 3.7 V at a current density of 5.4 mA/cm², a luminosity of 3,500 cd/m², a color coordinate of 0.33 and 0.62 and a luminescent efficiency of 68.7 cd/A.

Example 6

An OLED was manufactured in the same manner as in Example 1, except that Compound 15 was used instead of Compound 1 to form the ETL.

The OLED had high efficiency with a driving voltage of about 4.1 V at a current density of 5.9 mA/cm², a luminosity of 3,500 cd/m², a color coordinate of 0.31 and 0.60 and a luminescent efficiency of 66.6 cd/A.

Example 7

An OLED was manufactured in the same manner as in Example 1, except that Compound 18 was used instead of Compound 1 to form the ETL.

The OLED had high efficiency with a driving voltage of about 3.8 V at a current density of 5.5 mA/cm², a luminosity of 3,500 cd/m², a color coordinate of 0.32 and 0.60 and a luminescent efficiency of 72.4 cd/A.

Example 8

An OLED was manufactured in the same manner as in Example 1, except that Compound 23 was used instead of Compound 1 to form the ETL.

The OLED had high efficiency with a driving voltage of about 3.7 V at a current density of 5.4 mA/cm², a luminosity of 3,500 cd/m², a color coordinate of 0.32 and 0.62 and a luminescent efficiency of 65.5 cd/A.

Comparative Example

An OLED was manufactured in the same manner as in Example 1, except that the CBP was used instead of Compound 1 to form the EML.

The OLED had a driving voltage of about 5.1 V at a current density of 6.2 mA/cm², a luminosity of 3,500 cd/m², a color coordinate of 0.32 and 0.62 and a luminescent efficiency of 51.2 cd/A.

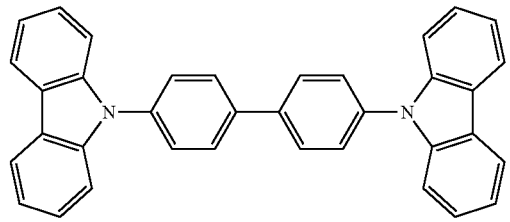

CBP

When the compound of Examples above was used as the phosphorescent host for the EML, compared to the CBP, the OLED including the compound had a driving voltage, which was decreased by more than 20%, and showed excellent I-V-L characteristics with greatly improved efficiency and improvement in lifetime. Results of representative lifetimes thereof are summarized and shown in Table 1 below:

TABLE 1

|  | Light-emitting material | T95 lifetime (hr @ 100 mA/cm²) |
| --- | --- | --- |
| Example 1 | Compound 1 | 397 hr |
| Example 2 | Compound 3 | 332 hr |
| Example 3 | Compound 5 | 275 hr |
| Example 4 | Compound 8 | 259 hr |
| Example 5 | Compound 11 | 264 hr |
| Example 6 | Compound 15 | 247 hr |
| Example 7 | Compound 18 | 219 hr |
| Example 8 | Compound 23 | 337 hr |
| Comparative Example 1 | CBP | 175 hr |

By way of summation and review, an important factor in determining a luminescent efficiency in an OLED is a light-emitting material, and a fluorescent material is has been used extensively. However, in terms of electroluminescence mechanism, the development of phosphorescent materials is one way to improve the luminescent efficiency, theoretically up to 4 times. Iridium III complex is a general phosphorescent light-emitting material, and (acac)Ir(btp)₂, Ir(ppy)₃, and Firpic may be used for each RGB.

As a host for phosphorescent light-emitting materials, CBP has been considered. A highly efficient OLED that has applied a hole blocking layer such as BCP and BAlq has been considered, and an advanced OLED using a BAlq derivative as a host has also been considered.

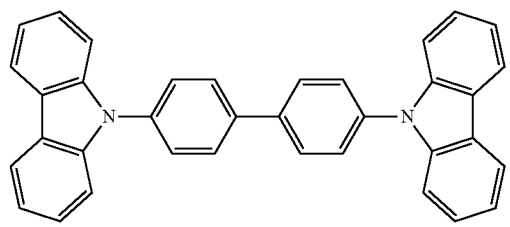

CBP

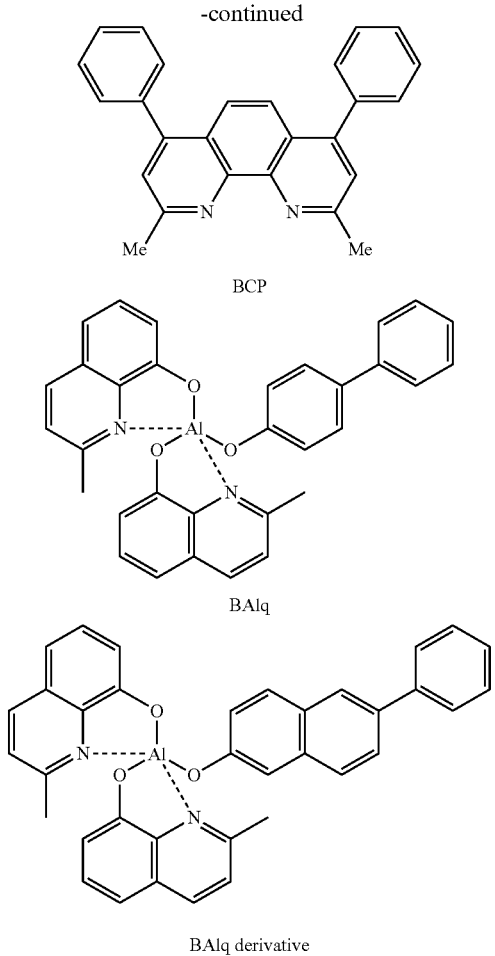

BCP

BAlq

BAlq derivative

Existing materials may have advantages in terms of light-emitting properties, but due to a low glass transition temperature and poor thermal stability, properties thereof may be changed during a high-temperature deposition process under vacuum conditions. An OLED is provided with a formula of power efficiency=(π/voltage)×current efficiency, wherein the power efficiency is inversely proportional to the voltage, and should be high to have an OLED with low-power consumption. An OLED using phosphorescent light-emitting materials may have a significantly higher current efficiency than an OLED using fluorescent materials. However, when materials such as BAlq and CBP are used as a host for phosphorescent light-emitting materials, an OLED using the same may have a high driving voltage. Thus, the OLED using phosphorescent light-emitting materials may not afford significant advantages in terms of power efficiency (lm/w) compared to the OLED using fluorescent light-emitting materials. Also, the OLED using phosphorescent light-emitting materials may exhibit shorter life time characteristics. Therefore, a host material that is more stable and has higher performance is of interest.

As described above, a compound of Formula 1 according to the example embodiment described above may provide excellent light-emitting capabilities, and may be suitable for fluorescent and phosphorescent devices, e.g., of green color. Therefore, an organic light-emitting device having high efficiency, low driving voltages, high luminance, and long lifetime may be manufactured using the compound.

Embodiments related to a compound and an organic light-emitting diode (OLED) including the same. The compound may provide better light-emitting capabilities and lifetime characteristics than existing host materials, and may be used as an organic light-emitting compound that may have an excellent framework with appropriate color coordinates. Therefore, an OLED using a compound according to an embodiment as an organic light-emitting material may exhibit high efficiency and long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Formula 1 below:

<Formula 1>

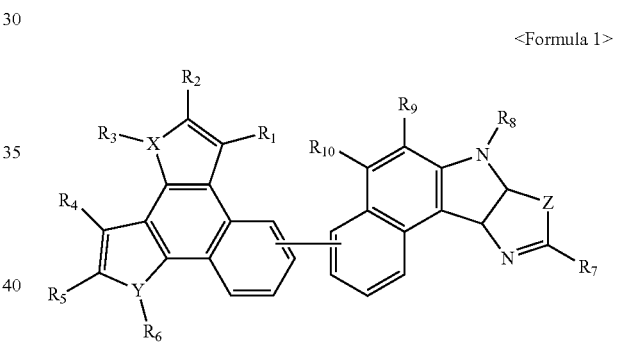

wherein, $R_1$ to $R_{10}$ are each independently a non-bonding electron pair, a hydrogen atom, a deuterium atom, a substituted or unsubstituted $C_1$-$C_{60}$ alkyl group, a substituted or unsubstituted $C_3$-$C_{60}$ cycloalkyl group, a substituted or unsubstituted $C_6$-$C_{60}$ aryl group, a substituted or unsubstituted $C_3$-$C_{60}$ heteroaryl group, or a substituted or unsubstituted $C_6$-$C_{60}$ condensed polycyclic group, X and Y are each independently N, S, or O, and Z is S or O.

2. The compound of claim 1, wherein $R_3$, $R_6$, $R_7$, and $R_8$ in Formula 1 each independently are one of the following compounds below:

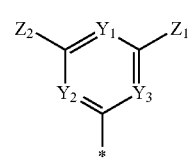

2a

-continued

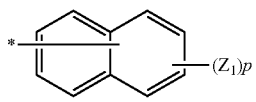
2b

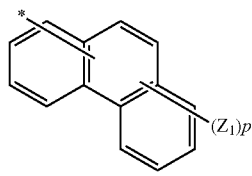
2c wherein, $Y_1$, $Y_2$, and $Y_3$ are each independently CH or N;

$Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, an amino group substituted with a $C_6$-$C_{20}$ aryl group or a $C_3$-$C_{20}$ heteroaryl group, a halogen atom, a cyano atom, a nitro group, a hydroxyl group, or a carboxyl group;

p is an integer from 1 to 9; and

* is a binding site.

3. The compound of claim 1, wherein $R_1$, $R_5$, and $R_{10}$ in Formula 1 are each independently a substituted or unsubstituted $C_1$-$C_{60}$ alkyl group.

4. The compound of claim 1, wherein $R_1$, $R_5$, and $R_{10}$ in Formula 1 are each independently a t-butyl group or a methyl group.

5. The compound of claim 1, wherein $R_2$, $R_4$, and $R_9$ in Formula 1 are each independently a hydrogen atom or a deuterium atom.

6. The compound of claim 1, wherein the compound of Formula 1 is one of the following compounds below:

-continued

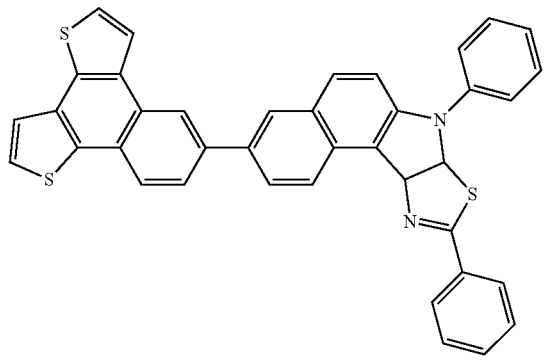
2

3

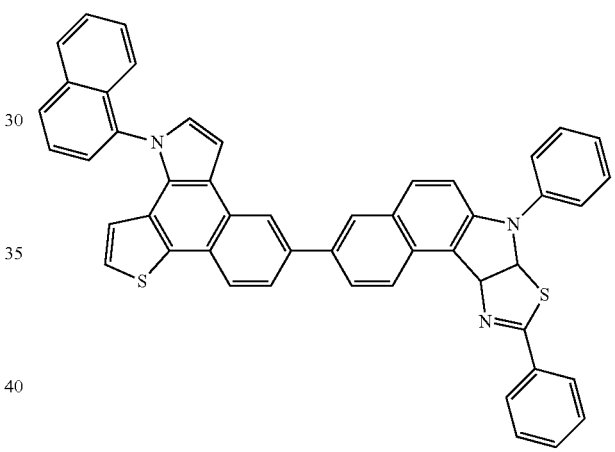
4

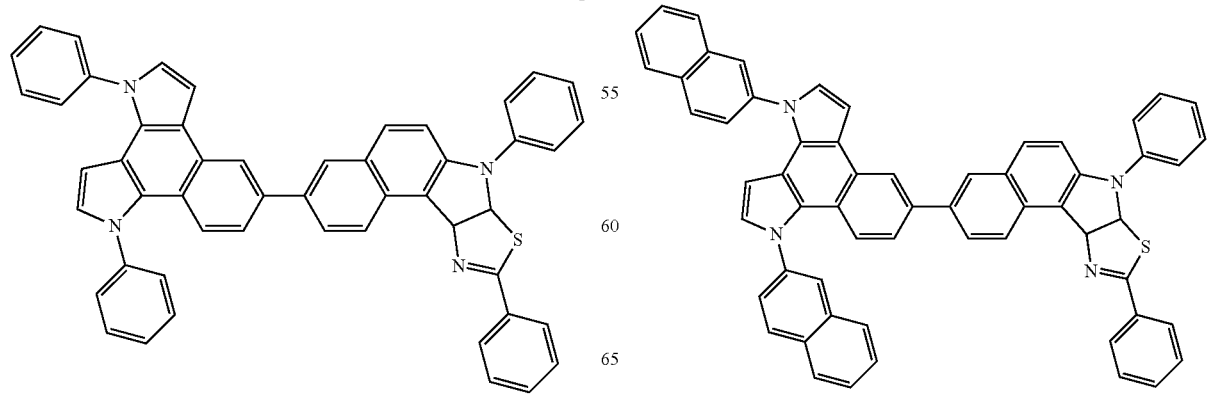
1

5
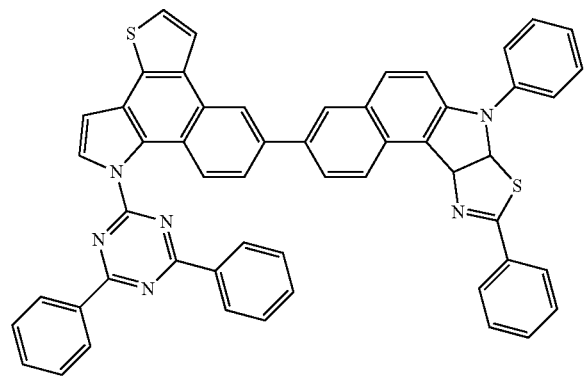
6
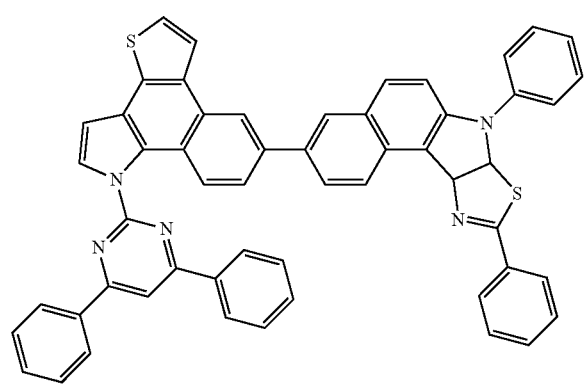
7
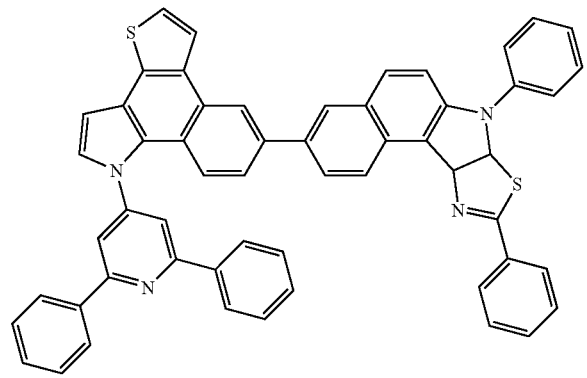
8
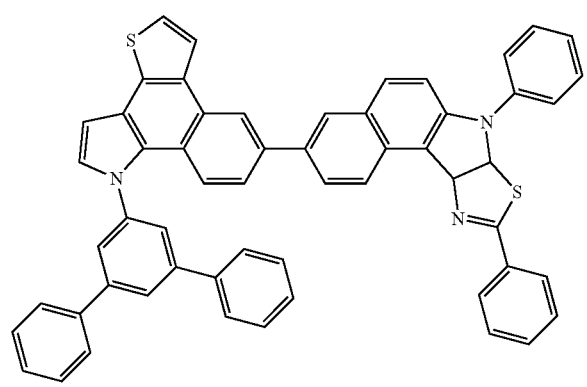
9
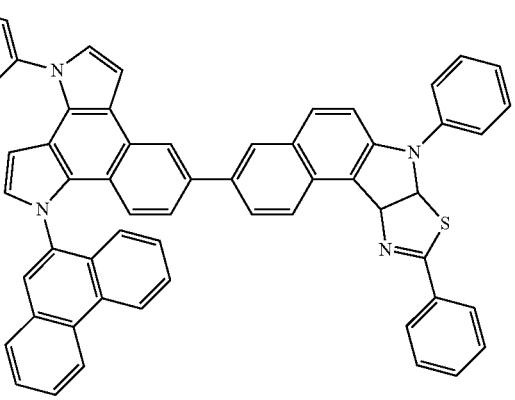
10
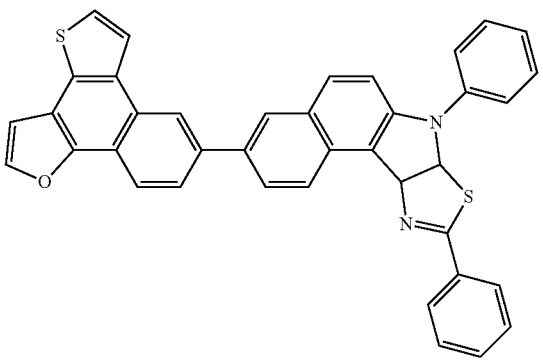
11
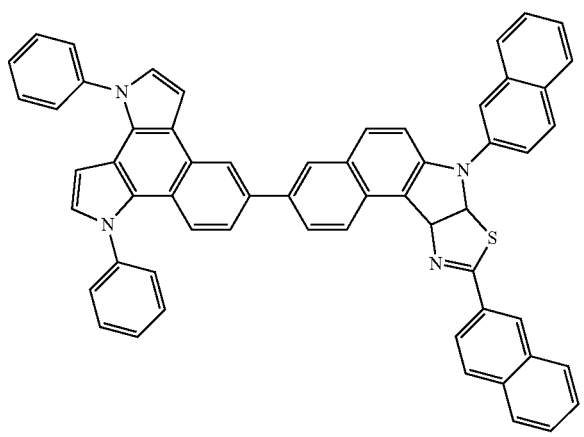
12
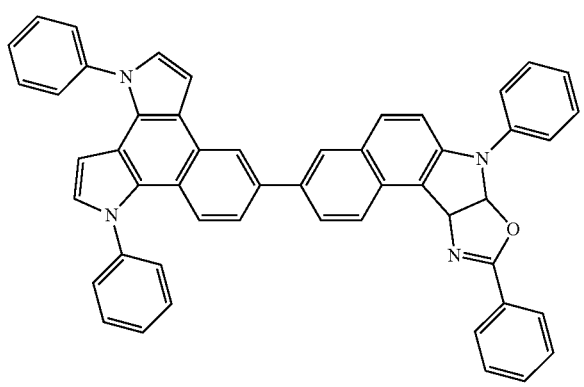

13
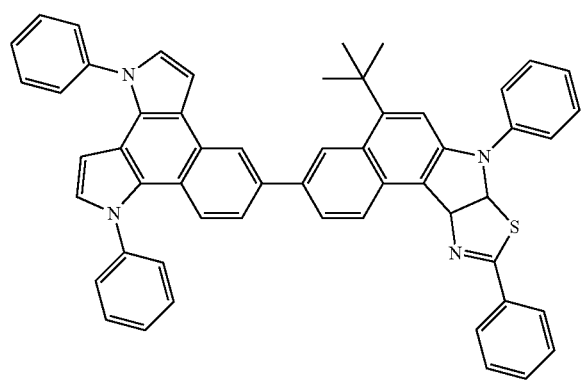
14
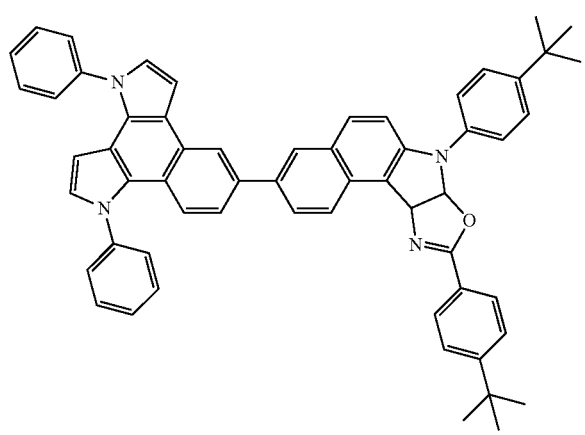
15
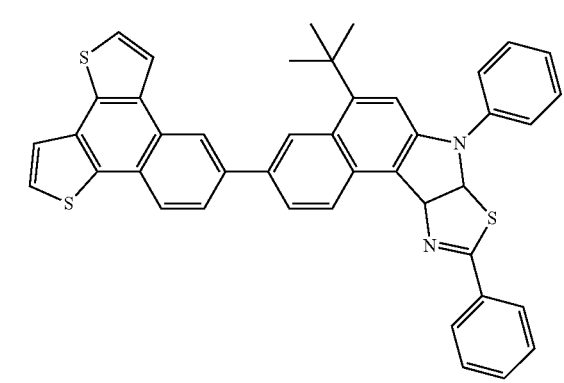

19

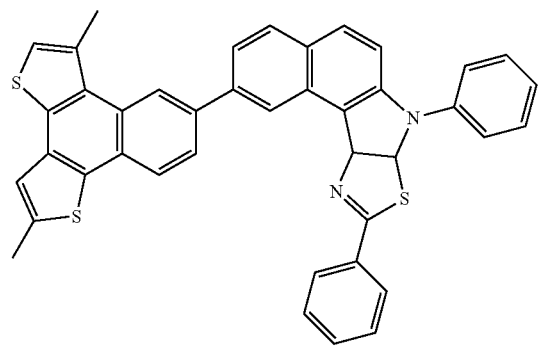

20

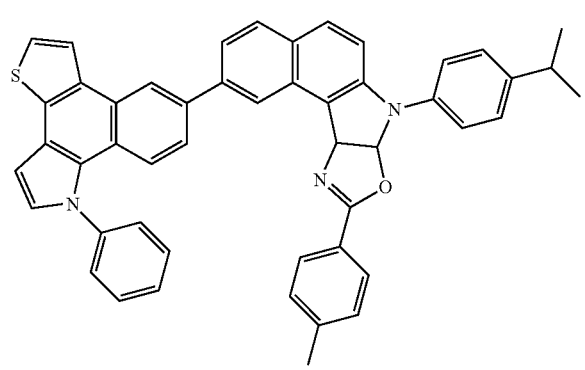

21

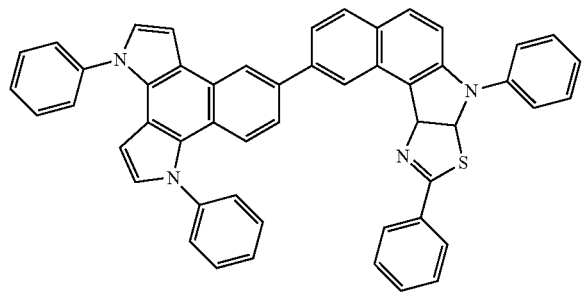

22

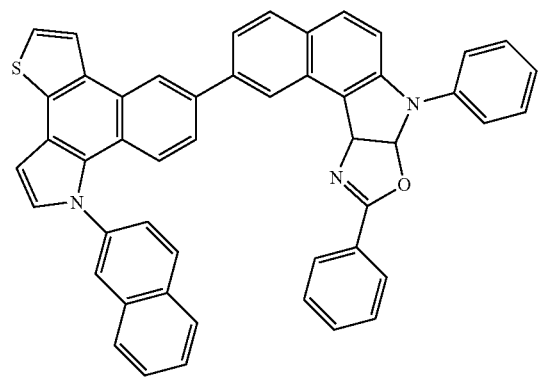

23

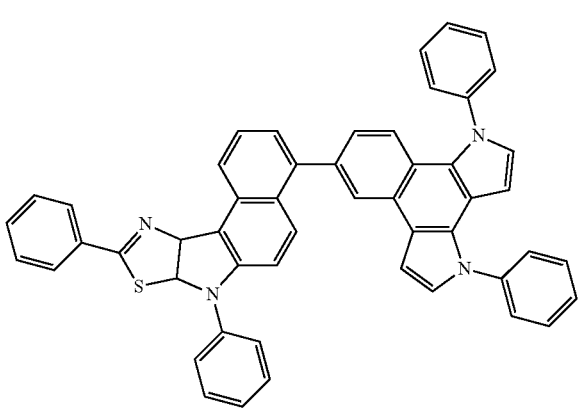

24

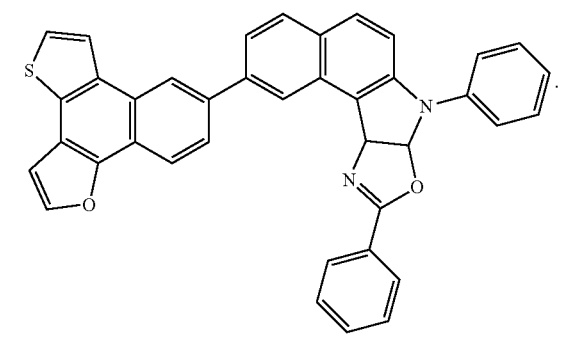

7. An organic light-emitting diode (OLED), comprising:
a first electrode;
a second electrode; and
an organic layer that is disposed between the first electrode and the second electrode, and includes the compound of claim 1.

8. The OLED of claim 7, wherein the organic layer is an emission layer.

9. The OLED of claim 7, wherein the organic layer is a green phosphorescent light-emitting layer.

10. The OLED of claim 7, wherein the organic layer is a green phosphorescent light-emitting layer, and the compound of Formula 1 is used as a host.

11. The OLED of claim 7, comprising:
an electron injection layer, an electron transport layer, a hole injection layer, a hole transport layer, or a functional layer having both hole injection and hole transport capabilities, and
an emission layer that includes the compound represented by Formula 1 and an anthracene-based compound.

12. The OLED of claim 7, comprising:
an electron injection layer, an electron transport layer, a hole injection layer, a hole transport layer, or a functional layer having both hole injection and hole transport capabilities, and
an emission layer that includes the compound represented by Formula 1 and an arylamine-based compound.

13. The OLED of claim 7, comprising:
an electron injection layer, an electron transport layer, a hole injection layer, a hole transport layer, or a functional layer having both hole injection and hole transport capabilities, and
an emission layer that includes the compound represented by Formula 1 and a styryl-based compound.

14. The OLED of claim 7, comprising:
an electron injection layer, an electron transport layer, a hole injection layer, a hole transport layer, or a functional layer having both hole injection and hole transport capabilities, and
an emission layer, wherein at least one of a red emission layer, a green emission layer, a blue emission layer, and a white emission layer of the emission layer includes a phosphorescent compound.

15. The OLED of claim 14, wherein the hole injection layer, the hole transport layer, or the functional layer having both hole injection and hole transport capabilities includes a charge-generating material.

16. The OLED of claim 15, wherein the charge-generating material is a p-dopant, and the p-dopant is a quinone derivative, a metal oxide, or a cyano group-containing compound.

17. The OLED of claim 7, wherein the organic layer includes an electron transport layer, and the electron transport layer includes an electron-transporting organic compound and a metal complex.

18. The OLED of claim 17, wherein the metal complex is a lithium complex.

19. The OLED of claim 7, wherein the organic layer is formed of the compound of claim 1 by using a wet process.

20. A flat panel display device comprising the OLED of claim 7,
wherein the first electrode of the OLED is electrically connected to a source electrode or a drain electrode in a thin film transistor.

* * * * *